US008722616B2

(12) United States Patent
Wang

(10) Patent No.: US 8,722,616 B2
(45) Date of Patent: May 13, 2014

(54) ANTI-HIV PEPTIDES AND METHODS OF USE THEREOF

(75) Inventor: Guangshun Wang, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 13/503,263

(22) PCT Filed: Oct. 19, 2010

(86) PCT No.: PCT/US2010/053137
§ 371 (c)(1),
(2), (4) Date: Jun. 4, 2012

(87) PCT Pub. No.: WO2011/049914
PCT Pub. Date: Apr. 28, 2011

(65) Prior Publication Data
US 2012/0237501 A1 Sep. 20, 2012

Related U.S. Application Data

(60) Provisional application No. 61/279,598, filed on Oct. 22, 2009, provisional application No. 61/258,400, filed on Nov. 5, 2009.

(51) Int. Cl.
*C07K 14/155* (2006.01)
*A61K 38/04* (2006.01)
*A61K 31/18* (2006.01)
*C07K 14/005* (2006.01)
*C07K 7/02* (2006.01)
*A61K 38/00* (2006.01)

(52) U.S. Cl.
CPC ............. *C07K 14/155* (2013.01); *C07K 14/005* (2013.01); *C07K 7/02* (2013.01); *A61K 38/00* (2013.01); *A61K 38/04* (2013.01); *A61K 31/18* (2013.01)
USPC ................. 514/1.1; 514/3.7; 514/3.8; 514/4.1

(58) Field of Classification Search
CPC ........ C07K 14/155; C07K 7/02; A61K 38/04; A61K 31/18; A61K 38/00
USPC ........................................... 514/3.7, 3.8, 4.1
See application file for complete search history.

(56) References Cited

U.S. PATENT DOCUMENTS

| 7,453,964 | B2 | 11/2008 | Pasqualini et al. |
| 7,465,784 | B2 | 12/2008 | Wang et al. |
| 7,985,836 | B2 | 7/2011 | Wang et al. |
| 2002/0151678 | A1 | 10/2002 | Arlinghaus |
| 2003/0022829 | A1 | 1/2003 | Maury et al. |
| 2004/0086535 | A1 | 5/2004 | Maury et al. |
| 2007/0037744 | A1 | 2/2007 | Gallo et al. |
| 2009/0005300 | A1 | 1/2009 | Hodges et al. |

FOREIGN PATENT DOCUMENTS

| WO | 2004/058789 | 7/2004 |
| WO | 2005/040192 | 5/2005 |
| WO | 2005/040201 | 5/2005 |
| WO | WO 2008086042 A2 * | 7/2008 |

OTHER PUBLICATIONS

GeneBank CAI99864.1. Jun. 3, 2006 .
Wang, G., et al. "Anti-human immunodeficiency virus type 1 activities of antimicrobial peptides derived from human and bovine cathelicidins." Antimicrob Agents Chemother. Sep. 2008;52(9):3438-40. Epub Jun. 30, 2008.
Steinstraesser, L., et al. "Inhibition of early steps in the lentiviral replication cycle by cathelicidin host defense peptides." Retrovirology. Jan. 18, 2005;2:2.
Bergman, P., et al. "The antimicrobial peptide LL-37 inhibits HIV-1 replication." Curr HIV Res. Jul. 2007;5(4):410-5.
Skerlavaj, B., et al. "Biological characterization of two novel cathelicidin-derived peptides and identification of structural requirements for their antimicrobial and cell lytic activities." J Biol Chem. Nov. 8, 1996;271(45):28375-81.
The Antimicrobial Peptide Database. <http://http://aps.unmc.edu/AP/main.php> Oct. 28, 2008.
Wang, G. "NMR Studies of a Model Antimicrobial Peptide in the Micelles of SDS, Dodecylphosphocholine, or Dioctanoylphosphatidylglycerol." Open Magnetic Resonance Journal. 2005;1:9-15.
Wang, G., et al. "APD2: the updated antimicrobial peptide database and its application in peptide design." Nucleic Acids Res. Jan. 2009;37(Database issue):D933-7. Epub Oct. 28, 2008.
Li, X., et al. "NMR studies of aurein 1.2 analogs." Biochim Biophys Acta. Sep. 2006;1758(9):1203-14. Epub Apr. 7, 2006.
Murakami, M., et al. "Postsecretory processing generates multiple cathelicidins for enhanced topical antimicrobial defense." J Immunol. Mar. 1, 2004;172(5):3070-7.
Li, X., et al. "Solution structures of human LL-37 fragments and NMR-based identification of a minimal membrane-targeting antimicrobial and anticancer region." J Am Chem Soc. May 3, 2006;128(17):5776-85.
Zanetti, M., et al. "Cathelicidins, multifunctional peptides of the innate immunity." J Leukoc Biol. Jan. 2004;75 (1):39-48. Epub Jul. 22, 2003.

* cited by examiner

*Primary Examiner* — Christina Bradley
*Assistant Examiner* — Kristina M Hellman
(74) *Attorney, Agent, or Firm* — Dann, Dorfman, Herrell & Skillman; Robert C. Netter, Jr.

(57) ABSTRACT

Anti-HIV peptides and methods of use are provided. In particular, these HIV inhibitory peptides are discovered based on the Antimicrobial Peptide Database.

17 Claims, 1 Drawing Sheet

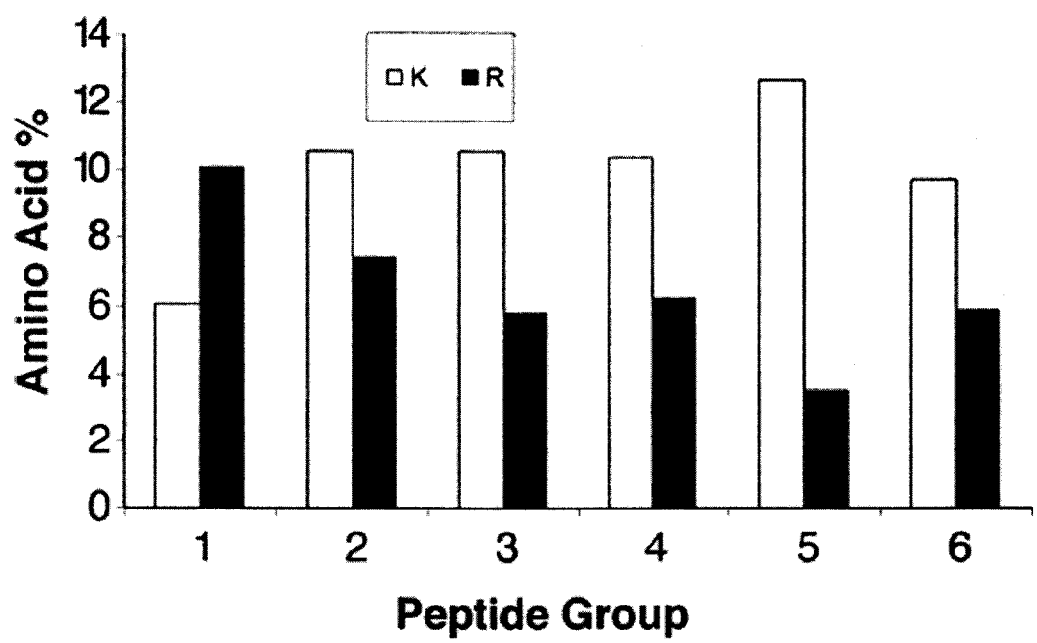

SEQUENCE LISTING

```
<160> NUMBER OF SEQ ID NOS: 68

<210> SEQ ID NO 1
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 1

Gly Trp Phe Asp Val Val Lys His Ile Ala Lys Arg Phe
1               5                   10

<210> SEQ ID NO 2
<211> LENGTH: 15
<212> TYPE: PRT
<213> ORGANISM: Palomena prasina

<400> SEQUENCE: 2

Val Asp Lys Pro Asp Tyr Arg Pro Arg Pro Arg Pro Pro Asn Met
1               5                   10                  15

<210> SEQ ID NO 3
<211> LENGTH: 14
<212> TYPE: PRT
<213> ORGANISM: Rana catesbeiana

<400> SEQUENCE: 3

Phe Leu Phe Pro Leu Ile Thr Ser Phe Leu Ser Lys Val Leu
1               5                   10

<210> SEQ ID NO 4
<211> LENGTH: 14
<212> TYPE: PRT
<213> ORGANISM: Vespa mandarinia

<400> SEQUENCE: 4

Ile Asn Leu Lys Ala Ile Ala Ala Leu Ala Lys Lys Leu Leu
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 5

Ile Lys Trp Lys Lys Leu Leu Arg Ala Ala Lys Arg Ile Leu
1               5                   10

<210> SEQ ID NO 6
<211> LENGTH: 14
<212> TYPE: PRT
<213> ORGANISM: Phyllomedusa hypochondrialis

<400> SEQUENCE: 6
```

```
Phe Arg Pro Ala Leu Ile Val Arg Thr Lys Gly Thr Arg Leu
  1               5                  10
```

```
<210> SEQ ID NO 7
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 7

Phe Phe Gly Lys Val Leu Lys Leu Ile Arg Lys Ile Phe
  1               5                  10
```

```
<210> SEQ ID NO 8
<211> LENGTH: 18
<212> TYPE: PRT
<213> ORGANISM: Apis mellifera L.

<400> SEQUENCE: 8

Gly Asn Asn Arg Pro Val Tyr Ile Pro Gln Pro Arg Pro Pro His Pro
  1               5                  10                  15

Arg Ile
```

```
<210> SEQ ID NO 9
<211> LENGTH: 19
<212> TYPE: PRT
<213> ORGANISM: Drosophila melanogaster

<400> SEQUENCE: 9

Gly Lys Pro Arg Pro Tyr Ser Pro Arg Pro Thr Ser His Pro Arg Pro
  1               5                  10                  15

Ile Arg Val
```

```
<210> SEQ ID NO 10
<211> LENGTH: 21
<212> TYPE: PRT
<213> ORGANISM: Xenopus laevis

<400> SEQUENCE: 10

Gly Met Ala Ser Lys Ala Gly Ala Ile Ala Gly Lys Ile Ala Lys Val
  1               5                  10                  15

Ala Leu Lys Ala Leu
                20
```

```
<210> SEQ ID NO 11
<211> LENGTH: 23
<212> TYPE: PRT
<213> ORGANISM: Styela clava

<400> SEQUENCE: 11

Val Phe Gln Phe Leu Gly Arg Ile Ile His His Val Gly Asn Phe Val
  1               5                  10                  15

His Gly Phe Ser His Val Phe
                20
```

```
<210> SEQ ID NO 12
<211> LENGTH: 21
<212> TYPE: PRT
<213> ORGANISM: Bufo gargarizans

<400> SEQUENCE: 12

Thr Arg Ser Ser Arg Ala Gly Leu Gln Phe Pro Val Gly Arg Val His
  1               5                  10                  15
```

```
Arg Leu Leu Arg Lys
        20

<210> SEQ ID NO 13
<211> LENGTH: 19
<212> TYPE: PRT
<213> ORGANISM: Styela clava

<400> SEQUENCE: 13

Gly Phe Gly Lys Ala Phe His Ser Val Ser Asn Phe Ala Lys Lys His
1               5                   10                  15

Lys Thr Ala

<210> SEQ ID NO 14
<211> LENGTH: 24
<212> TYPE: PRT
<213> ORGANISM: Pachycondyla goeldii

<400> SEQUENCE: 14

Leu Leu Lys Glu Leu Trp Thr Lys Ile Lys Gly Ala Gly Lys Ala Val
1               5                   10                  15

Leu Gly Lys Ile Lys Gly Leu Leu
        20

<210> SEQ ID NO 15
<211> LENGTH: 25
<212> TYPE: PRT
<213> ORGANISM: Pseudacanthotermes spiniger

<400> SEQUENCE: 15

His Val Asp Lys Lys Val Ala Asp Lys Val Leu Leu Leu Lys Gln Leu
1               5                   10                  15

Arg Ile Met Arg Leu Leu Thr Arg Leu
        20                  25

<210> SEQ ID NO 16
<211> LENGTH: 22
<212> TYPE: PRT
<213> ORGANISM: Morone saxatilis

<400> SEQUENCE: 16

Phe Phe His His Ile Phe Arg Gly Ile Val His Val Gly Lys Thr Ile
1               5                   10                  15

His Arg Leu Val Thr Gly
        20

<210> SEQ ID NO 17
<211> LENGTH: 24
<212> TYPE: PRT
<213> ORGANISM: Pseudis paradoxa

<400> SEQUENCE: 17

Gly Leu Asn Thr Leu Lys Lys Val Phe Gln Gly Leu His Glu Ala Ile
1               5                   10                  15

Lys Leu Ile Asn Asn His Val Gln
        20

<210> SEQ ID NO 18
<211> LENGTH: 21
<212> TYPE: PRT
<213> ORGANISM: Misgurnus anguillicaudatus

<400> SEQUENCE: 18
```

-continued

Arg Gln Arg Val Glu Glu Leu Ser Lys Phe Ser Lys Lys Gly Ala Ala
1               5                   10                  15

Ala Arg Arg Lys
            20

<210> SEQ ID NO 19
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 19

Asn Leu Val Ser Gly Leu Ile Glu Ala Arg Lys Tyr Leu Glu Gln Leu
1               5                   10                  15

His Arg Lys Leu Lys Asn Arg Lys Val
            20                  25

<210> SEQ ID NO 20
<211> LENGTH: 25
<212> TYPE: PRT
<213> ORGANISM: Lycosa carolinensis

<400> SEQUENCE: 20

Ile Trp Leu Thr Ala Leu Lys Phe Leu Gly Lys His Ala Ala Lys His
1               5                   10                  15

Leu Ala Lys Gln Gln Leu Ser Lys Leu
            20                  25

<210> SEQ ID NO 21
<211> LENGTH: 19
<212> TYPE: PRT
<213> ORGANISM: Parasilurus asotus

<400> SEQUENCE: 21

Lys Gly Arg Gly Lys Gln Gly Gly Lys Val Arg Ala Lys Ala Lys Thr
1               5                   10                  15

Arg Ser Ser

<210> SEQ ID NO 22
<211> LENGTH: 21
<212> TYPE: PRT
<213> ORGANISM: Rana septentrionalis

<400> SEQUENCE: 22

Gly Ile Trp Asp Thr Ile Lys Ser Met Gly Lys Val Phe Ala Gly Lys
1               5                   10                  15

Ile Leu Gln Asn Leu
            20

<210> SEQ ID NO 23
<211> LENGTH: 21
<212> TYPE: PRT
<213> ORGANISM: Litoria eucnemis

<400> SEQUENCE: 23

Gly Leu Leu Gly Leu Leu Gly Ser Val Val Ser His Val Val Pro Ala
1               5                   10                  15

Ile Val Gly His Phe
            20

<210> SEQ ID NO 24

```
<211> LENGTH: 20
<212> TYPE: PRT
<213> ORGANISM: Lachesana tarabaevi

<400> SEQUENCE: 24

Ser Trp Lys Ser Met Ala Lys Lys Leu Lys Glu Tyr Met Glu Lys Leu
 1               5                  10                  15

Lys Gln Arg Ala
            20

<210> SEQ ID NO 25
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 25

Gly Ala Trp Lys Asn Phe Trp Ser Ser Leu Arg Lys Gly Phe Tyr Asp
 1               5                  10                  15

Gly Glu Ala Gly Arg Ala Ile Arg Arg
            20                  25

<210> SEQ ID NO 26
<211> LENGTH: 19
<212> TYPE: PRT
<213> ORGANISM: Ascaphus truei

<400> SEQUENCE: 26

Gly Phe Lys Asp Leu Leu Lys Gly Ala Ala Lys Ala Leu Val Lys Thr
 1               5                  10                  15

Val Leu Phe

<210> SEQ ID NO 27
<211> LENGTH: 19
<212> TYPE: PRT
<213> ORGANISM: Crinia deserticola

<400> SEQUENCE: 27

Gly Leu Ala Asp Phe Leu Asn Lys Ala Val Gly Lys Val Val Asp Phe
 1               5                  10                  15

Val Lys Ser

<210> SEQ ID NO 28
<211> LENGTH: 18
<212> TYPE: PRT
<213> ORGANISM: Melecta albifrons

<400> SEQUENCE: 28

Gly Phe Leu Ser Ile Leu Lys Lys Val Leu Pro Lys Val Met Ala His
 1               5                  10                  15

Met Lys

<210> SEQ ID NO 29
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 29

Ser Leu Ser Arg Phe Leu Arg Phe Leu Lys Ile Val Tyr Arg Arg Ala
 1               5                  10                  15
```

Phe

<210> SEQ ID NO 30
<211> LENGTH: 23
<212> TYPE: PRT
<213> ORGANISM: bovine colostrum

<400> SEQUENCE: 30

Arg Pro Lys His Pro Ile Lys His Gln Gly Leu Pro Gln Glu Val Leu
1               5                   10                  15

Asn Glu Asn Leu Leu Arg Phe
            20

<210> SEQ ID NO 31
<211> LENGTH: 4
<212> TYPE: PRT
<213> ORGANISM: Artificial Sequence
<220> FEATURE:
<223> OTHER INFORMATION: Synthetic Sequence

<400> SEQUENCE: 31

Gly Leu Trp Glu
1

<210> SEQ ID NO 32
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 32

Gly Leu Phe Asp Ile Ile Lys Lys Ile Ala Glu Ser Trp
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 33

Gly Leu Trp Glu Lys Ile Asp Lys Phe Ala Ser Ile Ile
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 34

Gly Ile Ile Asp Ile Ala Lys Lys Leu Phe Glu Ser Trp
1               5                   10

<210> SEQ ID NO 35
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 35

Gly Trp Phe Asp Ile Ile Lys Lys Ile Ala Ser Glu Leu
1               5                   10

```
<210> SEQ ID NO 36
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 36

Gly Ile Phe Asp Lys Leu Ala Lys Glu Ile Ser Ile Trp
 1               5                  10

<210> SEQ ID NO 37
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 37

Gly Ile Trp Ser Asp Leu Ala Glu Ile Ile Lys Lys Phe
 1               5                  10

<210> SEQ ID NO 38
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 38

Gly Phe Leu Asp Ile Ile Glu Lys Ile Ala Lys Ser Trp
 1               5                  10

<210> SEQ ID NO 39
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 39

Gly Trp Leu Lys Lys Ile Glu Ser Ile Ile Asp Ala Phe
 1               5                  10

<210> SEQ ID NO 40
<211> LENGTH: 20
<212> TYPE: PRT
<213> ORGANISM: Bombina maxima

<400> SEQUENCE: 40

Ile Leu Gly Pro Val Leu Gly Leu Val Ser Asp Thr Leu Asp Asp Val
 1               5                  10                  15

Leu Gly Ile Leu
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 41

Ile Leu Gly Pro Val Leu Gly Leu Val Ser Arg Thr Leu Arg Arg Val
 1               5                  10                  15
```

```
Leu Gly Ile Leu
        20

<210> SEQ ID NO 42
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 42

Gly Phe Lys Arg Ile Val Gln Arg Ile Lys Asp Phe Leu Arg Asn Leu
1               5                   10                  15

Val

<210> SEQ ID NO 43
<211> LENGTH: 17
<212> TYPE: PRT
<213> ORGANISM: Artificial Sequence
<220> FEATURE:
<223> OTHER INFORMATION: Synthetic Sequence

<400> SEQUENCE: 43

Gly Phe Asn Glu Ile Val Gln Asp Ile Glu Asp Phe Leu Gln Asn Leu
1               5                   10                  15

Val

<210> SEQ ID NO 44
<211> LENGTH: 24
<212> TYPE: PRT
<213> ORGANISM: Phyllomedusa sauvagei

<400> SEQUENCE: 44

Gly Leu Arg Ser Lys Ile Trp Leu Trp Val Leu Leu Met Ile Trp Gln
1               5                   10                  15

Glu Ser Asn Lys Phe Lys Lys Met
        20

<210> SEQ ID NO 45
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 45

Gly Leu Arg Ser Arg Ile Trp Leu Trp Val Leu Leu Met Ile Trp Gln
1               5                   10                  15

Glu Ser Asn Arg Phe Lys Arg Met
        20

<210> SEQ ID NO 46
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 46

Gly Leu Lys Lys Leu Leu Gly Lys Leu Leu Lys Leu Gly Lys Leu
1               5                   10                  15

Leu Leu Lys

<210> SEQ ID NO 47
```

```
<211> LENGTH: 19
<212> TYPE: PRT
<213> ORGANISM: Artificial Sequence
<220> FEATURE:
<223> OTHER INFORMATION: Synthetic Sequence

<400> SEQUENCE: 47

Gly Leu Arg Arg Leu Leu Gly Arg Leu Leu Arg Arg Leu Gly Arg Leu
1               5                   10                  15

Leu Leu Arg

<210> SEQ ID NO 48
<211> LENGTH: 37
<212> TYPE: PRT
<213> ORGANISM: Artificial Sequence
<220> FEATURE:
<223> OTHER INFORMATION: Synthetic Sequence

<400> SEQUENCE: 48

Leu Leu Gly Asp Leu Leu Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 49
<211> LENGTH: 23
<212> TYPE: PRT
<213> ORGANISM: Artificial Sequence
<220> FEATURE:
<223> OTHER INFORMATION: Synthetic Sequence

<400> SEQUENCE: 49

Leu Leu Gly Asp Leu Leu Arg Lys Ser Lys Glu Lys Ile Gly Lys Glu
1               5                   10                  15

Phe Lys Arg Ile Val Gln Arg
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 50

Lys Arg Ile Val Gln Arg Ile Lys Asp Phe Leu Arg Asn Leu Val Pro
1               5                   10                  15

Arg Thr Glu Ser
        20

<210> SEQ ID NO 51
<211> LENGTH: 21
<212> TYPE: PRT
<213> ORGANISM: Artificial Sequence
<220> FEATURE:
<223> OTHER INFORMATION: Synthetic Sequence

<400> SEQUENCE: 51

Ser Lys Glu Lys Ile Gly Lys Glu Phe Lys Arg Ile Val Gln Arg Ile
1               5                   10                  15

Lys Asp Phe Leu Arg
        20
```

```
<210> SEQ ID NO 52
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 52

Phe Lys Arg Ile Val Gln Arg Ile Lys Asp Phe Leu Arg
 1               5                  10

<210> SEQ ID NO 53
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 53

Arg Leu Phe Asp Lys Ile Arg Gln Val Ile Arg Lys Phe
 1               5                  10

<210> SEQ ID NO 54
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 54

Lys Arg Ile Val Gln Arg Ile Lys Asp Phe Leu Arg
 1               5                  10

<210> SEQ ID NO 55
<211> LENGTH: 17
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: 9
<223> OTHER INFORMATION: D-amino acid

<400> SEQUENCE: 55

Gly Phe Lys Arg Ile Val Gln Arg Ile Lys Asp Phe Leu Arg Asn Leu
 1               5                  10                  15

Val

<210> SEQ ID NO 56
<211> LENGTH: 17
<212> TYPE: PRT
<213> ORGANISM: Articifial Sequence
<220> FEATURE:
<223> OTHER INFORMATION: Synthetic Sequence
<220> FEATURE:
<221> NAME/KEY: MOD_RES
<222> LOCATION: 9, 13
<223> OTHER INFORMATION: D-amino acid

<400> SEQUENCE: 56

Gly Phe Lys Arg Ile Val Gln Arg Ile Lys Asp Phe Leu Arg Asn Leu
 1               5                  10                  15

Val

<210> SEQ ID NO 57
<211> LENGTH: 20
```

```
<212> TYPE: PRT
<213> ORGANISM: Artificial Sequence
<220> FEATURE:
<223> OTHER INFORMATION: Synthetic Sequence

<400> SEQUENCE: 57

Gly Ile Lys Glu Phe Lys Arg Ile Val Gln Arg Ile Lys Asp Phe Leu
1               5                   10                  15

Arg Asn Leu Val
            20

<210> SEQ ID NO 58
<211> LENGTH: 20
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: (5)...(5)
<223> OTHER INFORMATION: Xaa = phenylglycine

<400> SEQUENCE: 58

Gly Ile Lys Glu Xaa Lys Arg Ile Val Gln Arg Ile Lys Asp Phe Leu
1               5                   10                  15

Arg Asn Leu Val
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 59

Gly Ile Lys Glu Trp Lys Arg Ile Val Gln Arg Ile Lys Asp Phe Leu
1               5                   10                  15

Arg Asn Leu Val
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 60

Gly Ile Lys Gln Phe Lys Arg Ile Val Gln Arg Ile Lys Asp Phe Leu
1               5                   10                  15

Arg Asn Leu Val
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 61

Gly Ile Lys Glu Phe Lys Arg Glu Phe Gln Arg Ile Lys Asp Phe Leu
1               5                   10                  15

Arg Asn Leu Val
            20
```

```
<210> SEQ ID NO 62
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 62

Gly Arg Phe Lys Arg Phe Arg Lys Lys Phe Lys Lys Leu Phe Lys Lys
  1               5                  10                  15

Ile Ser

<210> SEQ ID NO 63
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 63

Gly Arg Phe Lys Arg Phe Arg Lys Pro Phe Lys Lys Leu Phe Lys Lys
  1               5                  10                  15

Ile Ser

<210> SEQ ID NO 64
<211> LENGTH: 18
<212> TYPE: PRT
<213> ORGANISM: Artificial Sequence
<220> FEATURE:
<223> OTHER INFORMATION: Synthetic Sequence
<220> FEATURE:
<221> NAME/KEY: MOD_RES
<222> LOCATION: 6, 10
<223> OTHER INFORMATION: Xaa = phenylglycine

<400> SEQUENCE: 64

Gly Arg Phe Lys Arg Xaa Arg Lys Lys Xaa Lys Lys Leu Phe Lys Lys
  1               5                  10                  15

Ile Ser

<210> SEQ ID NO 65
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 65

Gly Arg Phe Lys Arg Ile Arg Lys Lys Leu Lys Lys Leu Phe Lys Lys
  1               5                  10                  15

Ile Ser

<210> SEQ ID NO 66
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 66

Gly Arg Phe Lys Arg Phe Arg Lys Lys Phe Lys Lys Leu Phe Lys
  1               5                  10                  15

<210> SEQ ID NO 67
```

```
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 67

Lys Lys Leu Leu Lys Lys Leu Lys Lys Leu Leu Lys
1               5                   10

<210> SEQ ID NO 68
<211> LENGTH: 18
<212> TYPE: PRT
<213> ORGANISM: Artificial Sequence
<220> FEATURE:
<223> OTHER INFORMATION: Synthetic Sequence

<400> SEQUENCE: 68

Gly Leu Phe Asp Ala Ala Lys Lys Ile Val Gly Lys Leu Ile Thr Ser
1               5                   10                  15

Leu Asn
```

ANTI-HIV PEPTIDES AND METHODS OF USE THEREOF

This application is a §371 application of PCT/US2010/053137, filed Oct. 19, 2010, which claims priority under 35 U.S.C. §119(e) to U.S. Provisional Patent Application No. 61/258,400, filed on Nov. 5, 2009, and U.S. Provisional Patent Application No. 61/279,598, filed on Oct. 22, 2009. The foregoing applications are incorporated by reference herein.

FIELD OF THE INVENTION

The present invention relates to the field of antimicrobial peptides and the treatment of microbial infections. More specifically the invention provides anti-HIV peptides, methods of identifying the same, and methods of using such peptides for the treatment of HIV infections.

BACKGROUND OF THE INVENTION

The acquired immunodeficiency syndrome (AIDS) has become the fourth leading cause of death worldwide and the majority of HIV infections are acquired through heterosexual intercourse. The United Nations estimates that there are now 40 million people living with HIV/AIDS. Thus, it is urgent to develop novel therapeutic and preventative agents. Because fully effective HIV vaccines are not yet available, development of topical microbicides that block the sexual transmission of HIV is also desirable (Buckheit, R. W. (2001) Expert Opin. Investig. Drugs, 10:1423-1442; Turpin, J. A. (2002) Expert Opin. Investig. Drugs, 11:1077-1097). Naturally occurring antimicrobial peptides (AMPs) are potent host defense molecules in all life forms (Zasloff et al. (2002) Nature 415:359-365; Jenssen et al. (2006) Clin. Microbial. Rev., 19:491-511; Lehrer, R.I. (2007) Curr. Opin. Hematol., 11:16-21). More than 1,500 such peptides have been registered in the antimicrobial peptide database (APD, aps.unmc.edu/AP/main.html; Wang and Wang (2004) Nucleic Acids Res., 32:D590-D592; Wang et al. (2009) Nucleic Acids Res., 37:D933-D937). Prior to this study, 68 peptide entries in the APD are known to have HIV inhibitory activity. Some typical examples are melittin, cecropin (Wachinger et al. (1998) J. Gen. Virol., 79:731-740), LL-37 (Bergman et al. (2007) Curr. HIV Res., 5:410-5; Wang et al. (2008) Antimicrob. Agents Chemother., 52:3438-3440), α, β, and θ-defensins (Cole, A. M. (2005) Protein Pept. Lett., 12:41-47; Lehrer, R. I. (2007) Curr. Opin. Hematol., 11:16-21), cyclotides (Ireland et al. (2008) Biopolymers 90:51-60), and indolicidin (Robinson et al. (1998) J. Leukoc. Biol., 63:94-100). Because only less than 5% of the AMPs in the database have been evaluated, the APD constitutes a useful source for identifying novel HIV-inhibitory peptides. This invention discloses a database-aided discovery of new anti-HIV peptides in three different approaches: database screening, peptide sequence shuffling, and database-knowledge-based peptide design, is shown hereinbelow.

SUMMARY OF THE INVENTION

In accordance with one aspect of the instant invention, anti-HIV peptides are provided. In a particular embodiment, the anti-HIV peptide has at least 90% homology with amino acid sequence GLRSRIWLWVLLMIWQESNRFKRM (SEQ ID NO: 45) or any HIV inhibitory peptide disclosed herein. Compositions comprising at least one anti-HIV peptide of the instant invention and at least one pharmaceutically acceptable carrier are also provided. The compositions may further comprise at least one anti-HIV compound.

In accordance with another aspect of the instant invention, method for inhibiting, treating, and/or preventing an HIV infection in a subject in need thereof are provided. The methods comprise administering to a subject at least one composition of the instant invention. In a particular embodiment, the methods further comprise at least one other anti-HIV treatment, such as the administration of at least one additional anti-HIV compound. Such combinatorial therapy leads to improved efficacy.

In accordance with another aspect of the instant invention, methods for increasing the anti-HIV activity of a peptide are provided. In a particular embodiment, the methods comprise increasing the number of arginines in a peptide.

BRIEF DESCRIPTIONS OF THE DRAWING

FIG. 1 provides a graph of the content of Lys (K) and Arg (R) residues in a group of antimicrobial peptides obtained from statistical analysis of the AMPs in the antimicrobial peptide database (aps.unmc.edu/AP/main.html). Group 1, 80 antiviral peptides; group 2, 405 antifungal peptides; group 3, 82 anticancer peptides; group 4, 1035 antibacterial peptides; group 5, 157 peptides that are toxic to mammalian cells; and group 6, all 1405 peptides analyzed.

DETAILED DESCRIPTION OF THE INVENTION

To identify novel anti-HIV peptides based on the antimicrobial peptide database (aps.unmc.edu/AP/main.php), 30 candidates were screened and 10 peptides were found with $EC_{50}$ concentrations (half maximal effective concentration; i.e., 50% inhibition of virus replication) <10 μM and therapeutic indices (TI) up to 17. For longer peptides such as human and bovine cathelicidins, anti-HIV peptide regions with improved TIs are identified. Furthermore, sequence shuffling of an aurein 1.2 analog generates a group of peptides with identical composition but different amino acid sequences. These peptides showed different HIV inhibitory activity. In addition, novel antimicrobial peptides such as GLK-19 are designed based on frequently occurring residues of the antimicrobial peptide database. Because antiviral peptides in the database have an arginine/lysine (R/K) ratio>1, an increase in the Arg content in maximin H5, dermaseptin S9, and GLK-19 improved their TIs. These examples demonstrate that the antimicrobial peptide database is a rich resource and useful tool for developing novel HIV-active peptides.

I. Definitions

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g., chromatographic methods, agarose or polyacrylamide gel electrophoresis, HPLC analysis, and the like).

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 10-30 or 15-25, or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 10-30 or 15-25, or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

Polymerase chain reaction (PCR) has been described in U.S. Pat. Nos. 4,683,195, 4,800,195, and 4,965,188, the entire disclosures of which are incorporated by reference herein.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., 1989, Molecular Cloning: A Laboratory Manual, Cold Spring Harbor Laboratory Press):

$$T_m=81.5° C.+16.6 \text{ Log } [Na+]+0.41(\% G+C)-0.63(\% \text{ formamide})-600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 μg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 μg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 μg/ml denatured salmon sperm DNA at 42° C., and washed in 0.1× SSC and 0.5% SDS at 65° C. for 15 minutes.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% or more by weight of the given compound. Purity is measured by methods appropriate for the given compound (e.g. chromatographic methods, agarose or polyacrylamide gel electrophoresis, HPLC analysis, and the like).

The term "gene" refers to a nucleic acid comprising an open reading frame encoding a polypeptide, including both exon and (optionally) intron sequences. The nucleic acid may also optionally include non-coding sequences such as promoter or enhancer sequences. The term "intron" refers to a DNA sequence present in a given gene that is not translated into protein and is generally found between exons.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween™ 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 20th Edition, (Lippincott, Williams and Wilkins), 2000; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

A "therapeutically effective amount" of a compound or a pharmaceutical composition refers to an amount effective to prevent, inhibit, treat, and/or lessen the symptoms of a particular disorder or disease. The treatment of a microbial infection (e.g., HIV infection) herein may refer to curing, relieving, and/or preventing the microbial infection, the symptom of it, or the predisposition towards it.

As used herein, an "anti-HIV compound" is a compound which inhibits HIV. Examples of an anti-HIV compound include, without limitation, (I) nucleoside-analog reverse transcriptase inhibitors (NRTIs; e.g., AZT (zidovudine, RETROVIR®), lamivudine (3TC, EPIVIR®), emtricitabine (EMTRIVA®), dideoxycytidine (ddC, zalcitabine, HIVID®), 2',3'-dideoxyinosine (ddI, VIDEX®), tenofovir DF (VIREAD®), stavudine (d4T, ZERIT®), abacavir (1592089; ZIAGEN®), adefovir dipivoxil (bis(POM)-PMEA; PREVON®), lobucavir (BMS-180194), BCH-10652, emtricitabine, elvucitabine, and lodenosine (FddA; 2'-beta-fluoro-2',3'-dideoxyadenosine)), (II) non-nucleoside reverse transcriptase inhibitors (NNRTIs; e.g., delavirdine (BHAP, U-90152; RESCRIPTOR®), efavirenz (DMP-266, SUSTIVA®), nevirapine (VIRAMUNE®), PNU-142721, capravirine (S-1153, AG-1549), emivirine (+)-calanolide A (NSC-675451) and B, etravirine (TMC-125), DAPY (TMC120), BILR-355 BS, PHI-236, and PHI-443 (TMC-278)), (III) protease inhibitors (PIs; e.g., amprenavir (141W94, AGENERASE®), tipranivir (PNU-140690, APTIVUS®), indinavir (MK-639; CRIXIVAN®), saquinavir (INVIRASE®, FORTOVASE®), fosamprenavir (LEXIVA®), lopinavir (ABT-378), ritonavir (ABT-538, NORVIR®), atazanavir (REYATAZ®), nelfinavir (AG-1343, VIRACEPT®), lasinavir (BMS-234475/CGP-61755), BMS-2322623, GW-640385X (VX-385), AG-001859, and SM-309515), and (IV) fusion inhibitors (FIs; e.g., T-20 (DP-178, FUZEON®) and T-1249). As used herein, the term "nucleoside-analog reverse transcriptase inhibitors" (NRTIs) refers to nucleosides and nucleotides and analogues thereof that inhibit the activity of HIV-1 reverse transcriptase. As used herein, NNRTIs are allosteric inhibitors which bind reversibly at a non-substrate-binding site on the HIV reverse transcriptase, thereby altering the shape of the active site or blocking polymerase activity. As used herein, the term "protease inhibitor" refers to inhibitors of the HIV-1 protease. As used herein, "fusion inhibitors" are compounds, such as peptides, which act by binding to HIV envelope protein and blocking the structural changes necessary for the virus to fuse with the host cell. Anti-HIV compounds also include HIV vaccines such as, without limitation, ALVAC® HIV (vCP1521), AIDSVAX®B/E (gp120), and combinations thereof. Anti-HIV compounds also include HIV antibodies (e.g., antibodies against gp120 or gp41 (e.g., VCR01 (Zhou et al. (Science (2010) 329:811-7), PG9 and PG16 (Doores et al. (J. Virol. (2010) 84:10510-21), and see also Walker et al. (Science (2009) 326:285-9), particularly broadly neutralizing antibodies.

As used herein, the term "antibiotic" refers to antimicrobial agents for use in mammalian, particularly human, therapy. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), polypeptides (e.g., colistin), and derivatives thereof.

II. Peptides

The anti-HIV peptides of the present invention may be prepared in a variety of ways, according to known methods. The anti-HIV peptides may be purified from appropriate sources (e.g., bacterial or animal cultured cells or tissues, optionally transformed) by immunoaffinity purification. The availability of nucleic acid molecules encoding the anti-HIV peptides enables production of the protein using in vitro expression methods and cell-free expression systems known in the art. In vitro transcription and translation systems are commercially available, e.g., from Promega™ Biotech (Madison, Wis.) or Gibco®-BRL (Gaithersburg, Md.).

Larger quantities of anti-HIV peptides may be produced by expression in a suitable prokaryotic or eukaryotic system. For example, part or all of a DNA molecule encoding for an anti-HIV peptide may be inserted into a plasmid vector adapted for expression in a bacterial cell, such as E. coli. Such vectors comprise the regulatory elements necessary for expression of the DNA in the host cell positioned in such a manner as to permit expression of the DNA in the host cell. Such regulatory elements required for expression include promoter sequences, transcription initiation sequences and, optionally, enhancer sequences.

Anti-HIV peptides produced by gene expression in a recombinant prokaryotic or eukaryotic system may be purified according to methods known in the art. A commercially available expression/secretion system can be used, whereby the recombinant protein is expressed and thereafter secreted from the host cell, and readily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus. Alternative tags may comprise the FLAG epitope or the hemaglutinin epitope. Such methods are commonly used by skilled practitioners.

The anti-HIV peptides of the instant invention may also be chemically synthesized. For example, the peptides may be synthesized using a solid-phase method. The chemically synthesized peptides may then be purified (e.g., by HPLC).

Anti-HIV peptides of the invention, prepared by the aforementioned methods, may be analyzed and verified according to standard procedures. For example, such protein may be subjected to amino acid sequence analysis, according to known methods.

Anti-HIV peptides are provided in the examples hereinbelow. Indeed, the instant invention encompasses any anti-HIV peptide described herein and their derivatives/variants, e.g., those derivatives/variants generated by sequence truncation, mutation, reversal, or shuffling. For example, the anti-HIV peptide of the instant invention may comprise SEQ ID NO: 1, SEQ ID NO: 3, SEQ ID NO: 7, SEQ ID NO: 11, SEQ ID NO: 14, SEQ ID NO: 15, SEQ ID NO: 16, SEQ ID NO: 22, SEQ ID NO: 23, SEQ ID NO: 26, SEQ ID NO: 28, SEQ ID NO: 29, SEQ ID NO: 32, SEQ ID NO: 34, SEQ ID NO: 35, SEQ ID NO: 37, SEQ ID NO: 38, SEQ ID NO: 39, SEQ ID NO: 41, SEQ ID NO: 42, SEQ ID NO: 45, SEQ ID NO: 47, SEQ ID NO: 48, SEQ ID NO: 52, SEQ ID NO: 57, SEQ ID NO: 59, SEQ ID NO: 60, SEQ ID NO: 61, SEQ ID NO: 62, SEQ ID NO: 63, or SEQ ID NO: 64. In a particular embodiment, the anti-HIV peptide of the instant invention comprises SEQ ID NO: 1, SEQ ID NO: 3, SEQ ID NO: 7, SEQ ID NO: 11, SEQ ID NO: 14, SEQ ID NO: 15, SEQ ID NO: 16, SEQ ID NO: 22, SEQ ID NO: 23, SEQ ID NO: 26, SEQ ID NO: 28, SEQ ID NO: 29, SEQ ID NO: 32, SEQ ID NO: 34, SEQ ID NO: 35, SEQ ID NO: 37, SEQ ID NO: 38, SEQ ID NO: 39, SEQ ID NO: 41, SEQ ID NO: 42, SEQ ID NO: 45, or SEQ ID NO: 47. In another embodiment, the anti-HIV peptide of the instant invention comprises SEQ ID NO: 7, SEQ ID NO: 14, SEQ ID NO: 15, SEQ ID NO: 29, SEQ ID NO: 42, SEQ ID NO: 45, or SEQ ID NO: 47. In another embodiment, the anti-HIV peptide of the instant invention comprises SEQ ID NO: 48, SEQ ID NO: 52, SEQ ID NO: 57, SEQ ID NO: 59, SEQ ID NO: 60, SEQ ID NO: 61, SEQ ID NO: 62, SEQ ID NO: 63, or SEQ ID NO: 64. In a particular embodiment, the anti-HIV peptide comprises at least one arginine substation and/or insertion. In still another embodiment, at least one lysine (e.g., all lysines) in the provided SEQ ID NO: is replaced with an arginine.

The amino acid sequence of the anti-HIV peptide of the instant invention may have at least 75%, 80%, 85%, 90%, 95%, 97%, 99%, or 100% homology with the above sequences, particularly at least 90% homology (e.g., the sequence may contain additions, deletions, and/or substitutions). In another embodiment, when the sequence of the anti-HIV peptide diverges from the above sequences, arginine has been inserted into the sequence and/or replaces a non-arginine amino acid of the provided sequence. In a particular embodiment, the anti-HIV peptide of the instant invention may extend beyond the above sequences at the amino and/or carboxy terminus by 1, 2, 3, 4, 5, 6, 7, 8, 9, or 10 amino acids, particularly by 1, 2, 3, 4, or 5 amino acids, particularly by 1, 2, or 3 amino acids. In yet another embodiment, the anti-HIV inhibitory peptides of the instant invention may also be in reverse orientation.

As stated hereinabove, the anti-HIV peptide of the instant invention may contain substitutions for the amino acids of the provided sequence. These substitutions may be similar to the amino acid (i.e., a conservative change) present in the provided sequence (e.g., an acidic amino acid in place of another acidic amino acid, a basic amino acid in place of a basic amino acid, a large hydrophobic amino acid in place of a large hydrophobic, etc.). The substitutions may also comprise amino acid analogs and mimetics. In a particular embodiment, the substitutions are predicted to promote helicity or helix formation. In yet another embodiment, an arginine residue is substituted for another amino acid within the provided sequence (e.g., an acidic amino acid or a lysine). As demonstrated herein, the amino acid sequences of HIV inhibitory peptides may be re-shuffled to improve activity.

The anti-HIV peptide of the instant invention may have capping, protecting and/or stabilizing moieties at the C-terminus and/or N-terminus. Such moieties are well known in the art and include, without limitation, amidation and acetylation. The peptide template may also be lipidated or glycosylated at any amino acid (i.e., a glycopeptide). In particular, these peptides may be PEGylated to improve druggability. The number of the PEG units ($NH_2(CH_2CH_2O)CH_2CH_2CO$) may vary, for example, from 1 to about 50.

The anti-HIV peptide of the instant invention may also comprise at least one D-amino acid instead of the native L-amino acid. The anti-HIV peptide may comprise only D-amino acids. In a particular embodiment, the anti-HIV peptides comprise D-amino acids which are spaced apart by about 1, 2, 3, and/or 4 (e.g., 3) consecutive L-amino acids.

The HIV-inhibitory peptides of the instant invention may contain at least one derivative of standard amino acids, such as, without limitation, fluorinated residues or nonstandard amino acids (e.g., beta-amino acids). In yet another embodiment, the peptide may also be circulated head to tail or locally involving a few residues.

In yet another embodiment of the instant invention, antimicrobial peptides are provided herein. In a particular embodiment, the anti-microbial peptide comprises SEQ ID NO: 67, 46, or 68. In a particular embodiment, the antimicrobial peptide comprises SEQ ID NO: 46. The antimicrobial peptides of the instant invention can be modified as described hereinabove for the anti-HIV peptides. In a particular embodiment, the peptides are modified to comprise lysines instead of arginines, as described hereinabove for the anti-HIV peptides (e.g., lysines are inserted into the peptides or substituted for non-lysine amino acids (e.g., arginine)). The present invention also encompasses nucleic acids encoding the peptides and pharmaceutical compositions comprising at least one antimicrobial peptide of the instant invention and at least one pharmaceutically acceptable carrier (see below). The present invention also encompasses methods for preventing, inhibiting, and/or treating microbial infections (as explained hereinbelow). The pharmaceutical compositions of the instant invention can be administered to an animal, in particular a mammal, more particularly a human, in order to treat/inhibit/prevent a microbial (e.g., *E. coli*, MRSA, etc.) infection (e.g., the composition may be administered before, during, or after a microbial infection). The pharmaceutical compositions of the instant invention may also comprise at least one other antimicrobial agent (e.g., an antibiotic). The additional antimicrobial agent may also be administered in a separate composition from the antimicrobial peptides of the instant invention. The compositions may be administered at the same time or at different times (e.g., sequentially).

III. Nucleic Acid Molecules

Nucleic acid molecules encoding the anti-HIV peptides of the invention may be prepared by any method known in the art such as (1) synthesis from appropriate nucleotide triphosphates or (2) isolation and/or amplification from biological sources. The availability of nucleotide sequence information enables preparation of an isolated nucleic acid molecule of the invention by oligonucleotide synthesis. Indeed, knowledge of the amino sequence is sufficient to determine an encoding nucleic acid molecule. Synthetic oligonucleotides may be prepared by the phosphoramidite method employed in the Applied Biosystems™ 38A DNA Synthesizer or similar devices. The resultant construct may be purified according to methods known in the art, such as gel electrophoresis or high performance liquid chromatography (HPLC).

Nucleic acid sequences encoding the anti-HIV peptides of the invention may be isolated from appropriate biological sources using methods known in the art. In one embodiment, a cDNA clone of the anti-HIV peptide is isolated from a cDNA expression library and modified, if necessary, to create the anti-HIV peptides of the instant invention. In an alternative embodiment, utilizing the sequence information provided by the cDNA sequence, genomic clones encoding anti-HIV peptides may be isolated.

Nucleic acids of the present invention may be maintained in any convenient vector, particularly an expression vector. Different promoters may be utilized to drive expression of the nucleic acid sequences based on the cell in which it is to be expressed. Antibiotic resistance markers are also included in these vectors to enable selection of transformed cells. Anti-HIV peptide encoding nucleic acid molecules of the invention include cDNA, genomic DNA, RNA, and fragments thereof which may be single- or double-stranded. Thus, this invention provides oligonucleotides having sequences capable of hybridizing with at least one sequence of a nucleic acid molecule of the present invention.

Also encompassed in the scope of the present invention are oligonucleotide probes which specifically hybridize with the anti-HIV peptide nucleic acid molecules of the invention. Primers capable of specifically amplifying anti-HIV peptides encoding nucleic acids described herein are also contemplated herein. Such oligonucleotides are useful as probes and primers for detecting, isolating or amplifying anti-HIV peptide encoding nucleic acids.

It will be appreciated by persons skilled in the art that variants (e.g., allelic variants) of the anti-HIV peptide sequences exist and may be taken into account when designing and/or utilizing oligonucleotides of the invention. Accordingly, it is within the scope of the present invention to encompass such variants, with respect to the anti-HIV peptide sequences disclosed herein or the oligonucleotides targeted to specific locations on the respective genes or RNA transcripts. Accordingly, the term "natural allelic variants" is used herein to refer to various specific nucleotide sequences of the invention and variants thereof that would occur in a population. The usage of different wobble codons and genetic polymorphisms which give rise to conservative or neutral amino acid substitutions in the encoded protein are examples of such variants. Such variants would not demonstrate substantially altered anti-HIV peptide activity or protein levels.

IV. Uses of the Anti-HIV Peptides

The present invention also encompasses pharmaceutical compositions comprising at least one anti-HIV peptide of the instant invention and at least one pharmaceutically acceptable carrier. Such a pharmaceutical composition may be administered, in a therapeutically effective amount, to a patient in need thereof. The pharmaceutical compositions of the present invention can be administered by any suitable route, for example, by injection (e.g., parenteral, intramuscular, intravenous, or intraperitoneal administration), by oral, pulmonary, nasal, topical, or other modes of administration such as controlled release devices. In general, pharmaceutical compositions and carriers of the present invention comprise, among other things, pharmaceutically acceptable diluents, preservatives, stabilizing agents, solubilizers, emulsifiers, adjuvants and/or carriers. Such compositions can include diluents of various buffer content (e.g., saline, Tris HCl, acetate, phosphate), pH and ionic strength; and additives such as detergents and solubilizing agents (e.g., Tween™ 80, Polysorbate 80), anti oxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. Exemplary pharmaceutical compositions and carriers are provided, e.g., in "Remington's Pharmaceutical Sciences" by E. W. Martin (Mack Pub. Co., Easton, Pa.) and "Remington: The Science And Practice Of Pharmacy" by Alfonso R. Gennaro (Lippincott Williams & Wilkins, 2005) which are herein incorporated by reference. The pharmaceutical composition of the present invention can be prepared, for example, in liquid form, or can be in pill or dried powder form (e.g., lyophilized).

In yet another embodiment, the pharmaceutical compositions of the present invention can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref. Biomed. Eng. (1987) 14:201; Buchwald et al., Surgery (1980) 88:507; Saudek et al., N. Engl. J. Med. (1989) 321: 574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105).

The present invention also encompasses methods for preventing, inhibiting, and/or treating microbial infections (e.g., viral (e.g., lentiviral) or bacterial), particularly HIV infections (e.g., HIV-1, HIV-2, etc.). The pharmaceutical compositions of the instant invention can be administered to an animal, in particular a mammal, more particularly a human, in order to treat/inhibit/prevent an HIV infection (e.g., the composition may be administered before, during, or after an HIV infection). The pharmaceutical compositions of the instant invention may also comprise at least one other anti-microbial agent, particularly at least one other anti-HIV compound/agent. The additional anti-HIV compound may also be administered in separate composition from the anti-HIV peptides of the instant invention. The compositions may be administered at the same time or at different times (e.g., sequentially).

The dosage ranges for the administration of the compositions of the invention are those large enough to produce the desired effect (e.g., curing, relieving, treating, and/or preventing the HIV infection, the symptoms of it (e.g., AIDS, ARC), or the predisposition towards it). The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications.

V. Methods for Generating Anti-HIV Peptides

The instant invention also encompasses methods for generating anti-HIV peptides. In a particular embodiment, the method comprises 1) obtaining a peptide; 2) increasing the number of basic amino acids (particularly arginine residues) in said peptide; and 3) determining the anti-HIV activity of the modified peptide. In one embodiment, the peptide is a known antimicrobial peptide prior to modification. For example, the peptide may be obtained from the antimicrobial peptide database (aps.unmc.edu/AP/main.html). In a particular embodiment, the anti-HIV activity of the modified peptide is compared to the anti-HIV activity of the unmodified peptide. The number of arginines in the peptide may be increased by adding/inserting arginines within and/or at the ends of the peptide or by substituting arginines for non-arginine amino acids in the peptide. In a particular embodiment, the lysines of the peptide are replaced with arginines. In another embodiment, acidic amino acids of the peptide are replaced with arginines. The anti-HIV activity of the modified peptides may be measured by any method, such as measuring the ability of the peptide to block the infection of cells by HIV.

In addition to the above and as described hereinbelow, anti-HIV peptides may also be generated by shuffling the sequence of a peptide, particularly an antimicrobial peptide (e.g., from the APD). The shuffled peptides can be analyzed as above with the arginine modified peptides.

In the case of longer antimicrobial peptides such as cathelicidins, the optimal HIV inhibitory regions can be identified by synthesizing multiple peptide fragments and comparing their activities.

This invention also illustrates de novo design of anti-HIV peptides based on the antimicrobial peptide database (aps.unmc.edu/AP/main.html) followed by peptide activity enhancement by substituting amino acids (e.g., lysines) to arginines.

The following examples describe illustrative methods of practicing the instant invention and are not intended to limit the scope of the invention in any way.

EXAMPLE 1

All the peptides were chemically synthesized using the solid-phase method and purified by HPLC to >95% (Genemed Synthesis, Inc., Tex.). Anti-HIV cytopathic effect inhibition assays were conducted as described (Buckheit et al. (1995) Antimicrob. Agents Chemother., 39:2718-2727). In brief, serially diluted peptides were added to a 96-well round bottom microtiter plate in triplicate. CEM-SS cells at a concentration of $2.5 \times 10^3$ cells per well and HIV-$1_{IIIB}$ at the appropriate pre-determined titer were sequentially added to the microtiter plate. The cultures were incubated at 5% $CO_2$/37° C. for six days. Following the incubation, the microtiter plates were stained with XTT tetrazolium dye to evaluate the efficacy and toxicity of the test compound(s). Using Microsoft Excel, $EC_{50}$ (50% inhibition of virus replication), $TC_{50}$ (50% reduction in cell viability) concentrations, and a therapeutic index (TI=$TC_{50}/EC_{50}$) are provided for each peptide.

To screen anti-HIV peptides based on the APD, 30 peptides (Table I) were selected with the aid of the search interface of the database. Peptides with the following known properties were rejected: (1) length >25 residues because it is less expensive to synthesize shorter peptides; (2) charge <0, as anionic peptides tend to be inactive; (3) Cys-containing, since peptides with multiple disulfide bonds are more costly to synthesize; (4) toxic to mammalian cells, since this is an undesired peptide property; (5) synthetic, as natural peptides were focused; and (6) known anti-HIV activity, since this will avoid duplicated effort. In addition, a representative member was selected when a family of peptides shared a similar sequence. Of the 30 peptides selected (Table 1), 13 originated from amphibians, eight from insects, three from fish, two from spiders, two from tunicates, one from cow, and one from bacteria. As detailed in the legend of Table 1, D70, D74, D76, and D9S are mutants of uperin 7.1, polybia-MPI, temporin-PTa, and temporin-LTc, respectively. These mutations were made in an attempt to enhance peptide activity based on a previous study (Wang et al. (2008) Antimicrob. Agents Chemother., 52:3438-3440). Eleven out of the 30 peptides were found to have $EC_{50}$ concentrations <10 μM. These include D70, D76, clavanin B, ponericin L2, spinigerin, piscidin 3, brevinin-2-related, maculatin 1.3, ascaphin-8, melectin, and D98. These peptides can be further grouped based on their therapeutic indices (TI). Of these 11 peptides, D76, D98, ponericin L2, and spinigerin have a TI>10. Because ponericin L2, and spinigerin displayed toxicity to human cells at 25 μM or greater, they are interesting templates for future peptide engineering.

TABLE 1

Database-based anti-HIV peptide screening.

| Name | Peptide Sequence | SEQ ID NO | EC$_{50}$ (μM) | TC$_{50}$ (μM) | TI |
|---|---|---|---|---|---|
| AZT | | | 0.009 | >0.5 | >55.6 |
| D70 (frog)[a] | GWFDVVKHIAKRF-NH$_2$ | 1 | 2.99 | 10.6 | 3.55 |
| Metalnikowin I (insect) | VDKPDYRPRPRPPNM | 2 | >54.4 | >54.4 | — |
| Ranatuerin 9 (frog) | FLFPLITSFLSKVL | 3 | 16.7 | 34.6 | 2.07 |
| Mastoparan M (insect)[b] | INLKAIAALAKKLL | 4 | >67.6 | >67.6 | — |
| D74 (insect)[c] | IKWKKLLRAAKRIL-NH$_2$ | 5 | >57.6 | 1.3 | <0.02 |
| Hyposin-5 (frog) | FRPALIVRTKGTRL | 6 | >61.4 | >61.4 | — |
| D76 (frog)[d] | FFGKVLKLIRKIF-NH$_2$ | 7 | 0.63 | 6.78 | 10.8 |
| Apidaecin IA (insect) | GNNRPVYIPQPRPPHPRI | 8 | >47.4 | >47.4 | — |
| Drosocin (insect)[e] | GKPRPYSPRPTSHPRPIRV | 9 | >45.5 | >45.5 | — |
| PGLa (frog) | GMASKAGAIAGKIAKVALKAL-NH$_2$ | 10 | >50.8 | >50.8 | — |
| Clavanin B (tunicate) | VFQFLGRIIHHVGNFVHGFSHVF | 11 | 7.1 | 37.1 | >5.18 |
| Buforin II (toad) | TRSSRAGLQFPVGRVHRLLRK | 12 | >41.1 | >41.1 | — |
| Styelin A (tunicate) | GFGKAFHSVSNFAKKHKTA-NH$_2$ | 13 | >48.5 | >48.5 | — |
| Ponericin L2 (insect) | LLKELWTKIKGAGKAVLGKIKGLL | 14 | 1.4 | 24.7 | 17.6 |
| Spinigerin (insect) | HVDKKVADKVLLLKQLRIMRLLTRL | 15 | 3.05 | >33.3 | >10.9 |
| Piscidin 1 (frog) | FFHHIFRGIVHVGKTIHRLVTG | 16 | 2.1 | 6.9 | 3.3 |
| Psuedin 1 (frog) | GLNTLKKVFQGLHEAIKLINNHVQ | 17 | 35.7 | >36.8 | >1.03 |
| Misgurin (fish) | RQRVEELSKFSKKGAAARRRK | 18 | >40.0 | >40.0 | — |
| D88 (frog)[f] | NLVSGLIEARKYLEQLHRKLKNRKV | 19 | >33.3 | >33.3 | — |
| Lycotoxin I (spider) | IWLTALKFLGKHAAKHLAKQQLSKL | 20 | >35.2 | 2.4 | <0.07 |
| Parasin I (fish) | KGRGKQGGKVRAKAKTRSS | 21 | >50.0 | >50.0 | — |
| Brevinin-2-related (frog) | GIWDTIKSMGKVFAGKILQNL-NH$_2$ | 22 | 1.65 | 7.42 | 4.49 |

TABLE 1-continued

Database-based anti-HIV peptide screening.

| Name | Peptide Sequence | SEQ ID NO | EC$_{50}$ (μM) | TC$_{50}$ (μM) | TI |
|---|---|---|---|---|---|
| Maculatin 1.3 (frog) | GLLGLLGSVVSHVVPAIVGHF-NH$_2$ | 23 | 4.0 | 8.02 | 2.01 |
| Latarcin 3a (spider) | SWKSMAKKLKEYMEKLKQRA | 24 | 32.7 | >40.3 | >1.23 |
| D94 (bacteria)[g] | GAWKNFWSSLRKGFYDGEAGRAIRR | 25 | >34.1 | >34.1 | — |
| Ascaphin-8 (frog) | GFKDLLKGAAKALVKTVLF-NH$_2$ | 26 | 1.2 | 2.9 | 2.4 |
| Desertcolin 1 (frog) | GLADFLNKAVGKVVDFVKS-NH$_2$ | 27 | >49.9 | >49.9 | — |
| Melectin (insect) | GFLSILKKVLPKVMAHMK-NH$_2$ | 28 | 4.34 | 7.75 | 1.79 |
| D98 (frog)[h] | SLSRFLRFLKIVYRRAF-NH$_2$ | 29 | 0.83 | 8.6 | 10.4 |
| Isracidin (cow) | RPKHPIKHQGLPQEVLNENLLRF | 30 | >36.2 | >36.2 | — |

[a]The peptides are chosen from the antimicrobial peptide database (Wang et al. (2004) Nuc. Acids Res., 32: D590-D592). D70 is a mutant where last three residues of uperin 7.1 were changed from SAV to KRF.
[b]C-terminal amidation is absent.
[c]A peptide mutant of polybia-MPI with the following mutations: D2K, D5R, and Q12R.
[d]A peptide mutant of temporin-PTa with S4K, P10R, and L13F mutations.
[e]Residue T11 is not o-glycosylated.
[f]The sequence of this peptide corresponds to chain A of distinction with residue C23 changed to R.
[g]The sequence of this peptide corresponds to chain a of plantaricin JK.
[h]A mutant of temporin-LTc with three mutations: S7R, P14R, and P15R.

Peptides with an EC$_{50}$>100 μg/ml (converted to μM in Table I) are defined as HIV inactive. They are metalnikowin I, mastoparan M, D74, hyposin-5, apidaecin IA, drosocin, PGLa, buforin II, styelin A, misgurin, D88, lycotoxin I, parasin I, plantaricin JK (chain A), desertcolin 1, and isacidin. Of these 16 peptides, insect-originated metalnikowin I, apidaecin IA, and drosocin are Pro-rich peptides. These antibacterial peptides could cross bacterial membranes and associate with heat-shock proteins (Otvos (2000) Biochem., 39:14150-14159). In contrast, buforin II can cross bacterial membranes and binds to DNA (Cho et al. (2009) Biochim. Biophys. Acta, 1788:1564-1569). The lack of toxicity of these peptides against HIV may be attributed to the absence of such molecular targets in the virus as well as the human cell. In addition, pseudin 1 and latarein 3a are essentially inactive against HIV with EC$_{50}$ close to 100 μg/ml.

Next, a Trp-containing aurein 1.2 (peptide B1 in Table 2) was used as a template to evaluate the effect of sequence shuffling on anti-HIV activity. Peptides B2-B8 were generated by re-arranging the 13 residues but reserving the potential of the sequence to form an amphipathic helix. In addition, each peptide was designed by mimicking a natural peptide in the database so that at least a few residues at the N-terminus of the peptides are shared with the model peptide (listed in the last column of Table 2). For example, peptide B2, with GLWE (SEQ ID NO: 31) as the N-terminal sequence, mimics the sequence pattern of caerin 3.2 from amphibians. The group B peptides were also subject to HIV inhibition evaluation. Peptides B1, B4, B6, and B7 showed similar EC$_{50}$. In particular, peptides B1 and B4 had essentially identical EC$_{50}$, TC$_{50}$, and TI. B4 was obtained primarily by swapping the positions between L2 and W13 of peptide B1. Peptides B6 and B7 showed improved TIs as a consequence of poor toxicity to the human cells. Peptides B3 and B8 show a simultaneous reduction in toxicity to the virus and the human cell. Finally, peptides B2 and B5 are rejected because they became nontoxic against HIV. Evidently, peptide sequence shuffling here led to the identification of B6 and B7 with improved TI values. Hence, sequence reshuffling expands the HIV-inhibitory peptide reservoir.

TABLE 2

Effects of sequence shuffling on HIV inhibitory activity of peptides in CEM-S cells.

| Name | Peptide Sequence | SEQ ID NO | $EC_{50}$ (μM) | $TC_{50}$ (μM) | TI | Peptide Modeled |
|---|---|---|---|---|---|---|
| AZT | | | 0.007 | >0.5 | >71.4 | |
| B1 | GLFDIIK KIAESW | 32 | 11.7 | 37.0 | 3.2 | Aurein 1.2 |
| B2 | GLWEKID KFASII | 33 | >65.8 | >65.8 | — | Caerin 3.2 |
| B3 | GIIDIAK KLFESW | 34 | 20.1 | >65.8 | >3.3 | Uperin 2.7 |
| B4 | GWFDIIK KIASEL | 35 | 10.7 | 38.9 | 3.6 | Uperin 7.1 |
| B5 | GIFDKLA KEISIW | 36 | >65.8 | >65.8 | — | Brevinin-2DYd |
| B6 | GIWSDLA EIIKKF | 37 | 11.4 | >65.8 | >5.8 | Ponericin W3 |
| B7 | GFLDIIE KIAKSW | 38 | 10.5 | >65.8 | >6.3 | Ranatuerin 3 |
| B8 | GWLKKIE SIIDAF | 39 | 29.5 | >65.8 | 2.2 | Cecropin |

As a third approach, the anti-HIV activity of antimicrobial peptides was improved based on findings from the database. A statistical analysis of antimicrobial peptides in the database led to the identification of the frequently occurring amino acids (>10%) in different kingdoms (Wang et al. (2009) Nuc. Acids Res., 37:D933-D937). For example, residues Gly and Cys are abundant in plant peptides, while residues Gly, Ala, Leu, and Lys are rich in amphibian peptides. Further investigation reveals that the percentage of arginines in antiviral peptides is highest, compared to antibacterial, antifungal, or anticancer peptides (FIG. 1), where the percentage of Lys is always higher than that of Arg. This observation may be used to enhance the anti-HIV activity of AMPs. Maximin H5 is an anionic peptide and was found to be inactive against HIV-$1_{III}$ (Table 3). However, the peptide became HIV inhibitory when the three acidic Asp residues were converted to basic Arg residues. Consistent with this observation, it was determined that GF-17, a human LL-37-derived HIV-active peptide (Wang et al. (2008) Antimicrob. Agents Chemother., 52:3438-3440), lost its anti-HIV activity when an acidic version of the peptide was synthesized (Table 3). These examples indicate that positively charged residues in AMPs play an important role in HIV inhibition.

TABLE 3

Effects of charge and cationic residue types on HIV inhibitory activity of antimicrobial peptides and their analogs in CEM-SS cells.

| Peptide Name | Peptide Sequence | SEQ ID NO | $EC_{50}$ (μM) | $TC_{50}$ (μM) | TI |
|---|---|---|---|---|---|
| AZT | | | 0.007 | >0.5 | >71.4 |
| Maximin H5 | ILGPVLGLVSD TLDDVLGIL | 40 | >49.4 | >49.4 | — |
| Maximin H5r3 | ILGPVLGLVSR TLRRVLGIL | 41 | 2.2 | 8.7 | 3.9 |
| GF17 | GFKRIVQRIKD FLRNLV | 42 | 0.76 | 10.8 | 14.2 |
| GF17- | GFNEIVQDIED FLQNLV | 43 | >25.1 | >25.1 | — |
| DRS S9 | GLRSKIWLWVLLM IWQESNKFKKM | 44 | 31.6 | >32.9 | >1.04 |
| DRS S9r3 | GLRSRIWLWVLLM IWQESNRFKRM | 45 | 1.25 | >32.1 | >25.7 |
| GLK-19 | GLKKLLGKLLKKL GKLLLK | 46 | >47.5 | 25.1 | <0.5 |
| GLR-19 | GLRRLLGRLLRRL GRLLLR | 47 | 4.4 | 25.7 | 5.8 |

To illustrate the importance of Arg residues, a dermaseptin (DRS) S9 mutant was synthesized by replacing three lysines with arginines (Table 3). While wild type DRS S9 showed a very weak activity against HIV, the HIV inhibitory activity of the arginine mutant DRS S9r3 is much higher with a TI of ~26. As another example, GLK-19, which was designed based on the three frequently occurring residues Gly, Leu, and Lys residues from animal AMPs (Wang et al. (2009) Nuc. Acids Res., 37:D933-D937), was evaluated. Although the peptide showed higher antibacterial activity against *E. coli* K17 than human LL-37, it displayed no activity against HIV. After changing all Lys residues to Arg, however, the resulting peptide (GLR-19) became HIV active (Table 3). These examples indicate that an increase in arginine content in antimicrobial peptides improves the potency of the peptide against HIV.

Thus, the instant study demonstrates database-aided anti-HIV peptide discovery by different strategies. First, a select set of peptides from the APD can be directly screened for anti-HIV activity, allowing for the identification of better peptide templates. Although only 30 peptides were screened, the success rate is high (37%). Second, additional HIV-active peptides can be generated via sequence reshuffling (i.e., sequence rearrangements of the same peptide). From merely eight peptides synthesized, two peptides were identified with the therapeutic index nearly doubling. Third, database-derived knowledge can also be utilized to improve the therapeutic index of the peptide. Because of the higher Arg/Lys ratio in antiviral peptides, it was possible to improve HIV inhibitory activity in several cases by increasing the Arg content. These examples prove that the antimicrobial peptide database (Wang et al. (2004) Nuc. Acids Res., 32:D590-D592) provides a rich source for engineering novel anti-HIV peptides.

EXAMPLE 2

In mammals, defensins and cathelicidins are the two major classes of antimicrobial peptides. While the three types of defensins, the α-, β-, and θ-defensins, contain several β strands, which are further stabilized by three pairs of disulfide bonds, the cathelicidins vary in both their sequences and their three-dimensional structures (usually extended or α-helical structures). Another important difference is that there are at least 10 different defensins in humans, but only one cathelicidin (LL-37) has been identified (Wang, G. (2007) Protein Pept. Lett., 14:57-69; Zanetti, M. (2004) J. Leukoc. Biol., 75:39-48). All human α-defensins and human β-defensin-3 inhibit HIV infection (Hazrati et al. (2006) J. Immunol., 177: 8658-8666), but the θ-defensins are more effective (Cole et al. (2002) Proc. Natl. Acad. Sci., 99:1813-1818; Cordes et al. (2002) J. Mol. Biol., 323:951-960; Munk et al. (2003) AIDS Res. Hum. Retrovir., 19:875-881; Wang et al. (2003) J. Immunol., 170:4708-4716; Wang et al. (2004) J. Immunol., 173:515-520). Furthermore, retrocyclin-2 is much more powerful than retrocyclin-1 against HIV-1 subtypes A, B, and C. Retrocyclins as well as human α-defensins 1-3 are lectins that bind gp120 with high affinity (Wang et al. (2004) J. Immunol., 173:515-520). Importantly, retrocyclins appear to have little cytotoxicity on H9 cells and cervical carcinoma cells (Cole et al. (2008) Am. J. Reproductive Immunol., 59:27-34).

There are three families of cathelicidins found in animals, fish, and birds. The first family of peptides, such as human LL-37, tends to form an α-helical structure; the second family of peptides such as protegrins possesses a β-sheet structure, which is stabilized by intramolecular disulfide bonds. Finally, the third peptide family is known to be rich in certain amino acids. While PR-39 is rich in prolines and arginines, bovine indolicidin is a Trp- and Pro-rich peptide. Cathelicidins have been shown to have a broad range of effects on bacteria, fungi, viruses, and parasites (Zanetti, M. (2004) J. Leukoc. Biol., 75:39-48). Among them, LL-37 (Bergman et al. (2007) Curr. HIV Res., 5:410-415), protegrin-1 (Steinstraesser et al. (2005) Retrovirology 2:1-12), and indolicidin (Marchand et al. (2006) Nucleic Acids Res., 34:5157-5165; Robinson et al. (1998) J. Leukoc. Biol., 63:94-100) have been demonstrated to have anti-HIV activities, albeit a relatively high concentration of indolicidin is required (333 μg/ml) to be effective. It was shown that indolicidin interferes with formation of the catalytic integrase-DNA complex directly binding to DNA (Marchand et al. (2006) Nucleic Acids Res., 34:5157-5165).

As the only cathelicidin in humans, LL-37 can be cleaved in vivo into active fragments. While KS-30, KR-20, and RK-31 were identified in human sweat, LL-23, KS-27, and LL-29 were detected in human skin (Murakami et al. (2004) J. Immunol., 172:3070-3077; Yamasaki et al. (2006) FASEB J., 20:2068-2080). These peptides are named in the same manner as LL-37 by starting with the first two amino acid residues in the one-letter code followed by the number of residues in the peptide. In addition to the natural fragments of LL-37, several labs searched for the active regions by in vitro experiments with a goal of engineering new peptides of therapeutic value based on the identified peptide templates (Braff et al. (2005) J. Immunol., 174:4271-4278; Nagaoka et al. (2002) Clin. Diagn. Lab. Immunol., 9:972-982; Nell et al. (2006) Peptides 27:649-660; Wang, G. (2007) Protein Pept. Lett., 14:57-69). Using nuclear magnetic resonance spectroscopy, a minimally antimicrobial and anticancer region was identified corresponding to residues 17 to 29 (FK-13) (Li et al. (2006) J. Am. Chem. Soc., 128:5776-5785). The identification of the minimal active peptide region facilitates peptide synthesis and mutational studies. The LL-37 peptides identified in vivo or in vitro were found to be bactericidal. Their anti-HIV activities, however, have not yet been evaluated. Here, the anti-HIV activities of 20 synthetic peptides (>95% purity; Genemed Synthesis, Inc.) derived from human and bovine cathelicidins are provided.

Materials and Methods

Peptides: Twenty peptides were chemically synthesized and purified by reverse-phase HPLC. Peptide purity was greater than 95%. For all synthetic peptides that do not have the original C-terminal residue of either LL-37 or BMAP-27, amidation was performed to improve peptide stability and perhaps biological activity.

Anti-HIV Assays in Fresh Human PBMCs Utilizing Low Passage Clinical Viruses: Fresh human peripheral blood mononuclear cells (PBMCs) determined to be seronegative for HIV were isolated using Ficoll-Hypaque methodology. Assays were initiated with PBMCs that had been induced to proliferate with PHA-P for 72 hours. For the PBMC assay, PHA-P stimulated PBMCs from three donors were pooled, suspended in fresh tissue culture medium at $1 \times 10^6$ cells/mL and plated in the interior wells of a 96-well round bottom microtiter plate at 50 μl/well. One hundred microliters (100 μL) of 2 times the concentration of compound-containing medium was transferred to the round-bottom 96-well plate containing the cells.

Immediately following addition of test materials to the wells, 50 μL of a HIV-$1_{HT/92/599}$ at a pre-determined titer was added and wells mixed. PBMCs were exposed in triplicate to virus and cultured in the presence or absence of the test material at varying concentrations. After 7 days in culture, HIV-1 replication was quantified by the measurement of cell-free HIV-1 reverse transcriptase (RT) activity in the tissue culture supernatant. Wells with cells and virus alone were used as virus controls. Separate plates were identically prepared without virus for drug cytotoxicity evaluation using the tetrazolium dye XTT (2,3-bis(2-methoxy-4-nitro-5-sulfophenyl)-5-[(phenylamino)carbonyl]-2H-tetrazolium hydroxide).

Cytopathic Effect (CPE) Inhibition Assay: The CPE assay was performed as previously described (Buckheit et al. (1995) Antimicrob. Agents Chemother., 39:2718-2727). Briefly, serially diluted compound was added to a 96-well round bottom microtiter plate in triplicate. CEM-SS cells at a concentration of $2.5 \times 10^3$ cells per well and HIV-$1_{IIIB}$ at the appropriate pre-determined titer were sequentially added to the microtiter plate. The cultures were incubated at 5% $CO_2$/37° C. for six days. Following the incubation, the microtiter plates were stained with XTT tetrazolium dye to evaluate the efficacy and toxicity of the test compound(s).

Data Analysis and Evaluation: Using Microsoft Excel, $EC_{50}$ (50% inhibition of virus replication), and $IC_{50}$ (50% reduction in cell viability) concentrations as well as a therapeutic index (TI=$TC_{50}/EC_{50}$) were obtained.

Results

Before the anti-HIV effect of LL-37 fragments was investigated, the anti-HIV effect of full-length LL-37 was tested in parallel with the positive control AZT, a nucleoside reverse transcriptase inhibitor (Glaxo Wellcome). As reported in Table 4, synthetic LL-37 was determined to be active against HIV type I (HIV-$1_{IIIB}$) with an $EC_{50}$ concentration of 7.3 μg/mL and a TI of approximately 11. This finding is consistent with the findings of Bergman et al. (Curr. HIV Res. (2007) 5:410-415).

To locate the HIV-inhibitory region(s) in human LL-37, anti-HIV assays were performed (see Table 4) for a select set of peptide fragments, which had been identified in vivo and in vitro. Among the several protease-generated natural peptides (Murakami et al. (2004) J. Immunol., 172:3070-3077; Yamasaki et al. (2006) FASEB J. 20:2068-2080), the antiviral effects of LL-23 and KR-20 were evaluated, which correspond to the N- and C-terminal fragments of human LL-37, respectively. Neither LL-23 nor KR-20 showed an effect on the virus even at a high peptide concentration of 100 μg/mL, which is defined as being inactive in subsequent assays. These results indicate that the HIV-active region of LL-37 is located in the middle region of the peptide. To test this possibility, SK-21 was synthesized by truncating eight residues from both ends of LL-37. Anti-HIV assays revealed that SK-21 was active ($EC_{50}$=28.5 μg/mL), although its antiviral potency was not as high as the parent molecule (Table 4).

TABLE 4

Anti-HIV activities of human cathelicidin LL-37-derived peptides in CEM-SS cells[a].

| Peptide name | Peptide sequence[b] | $EC_{50}$ (μM) | $TC_{50}$ (μM) | TI | SEQ ID NO |
|---|---|---|---|---|---|
| LL-37 | LLGDLLRKSKEKIGKEFKRIVQRIKDFLRNLVPRTES | 1.6 | 18.4 | 11.5 | 48 |
| LL-23 | LLGDLLRKSKEKIGKEFKRIVQR | >35.4 | >35.4 | — | 49 |
| KR-20 | KRIVQRIKDFLRNLVPRTES | >40.5 | >40.5 | — | 50 |
| SK-21 | SKEKIGKEFKRIVQRIKDFLR | 10.8 | 22.5 | 2.08 | 51 |
| FK-13 | FKRIVQRIKDFLR | 3.4 | 10.4 | 3.1 | 52 |
| Retro-FK13 | RLFDKIRQVIRKF | >58.1 | 33.7 | — | 53 |
| KR-12 | KRIVQRIKDFLR | >63.5 | >63.5 | — | 54 |
| GF-17 | GFKRIVQRIKDFLRNLV | 0.98 | 8.9 | 9.1 | 42 |
| GF-17$_{d1}$[c] | GFKRIVQRIKDFLRNLV | >47.5 | 22.7 | — | 55 |
| GF-17$_{d2}$ | GFKRIVQRIKDFLRNLV | >47.5 | >47.5 | — | 56 |
| GI-20 | GIKEFKRIVQRIKDFLRNLV | 1.08 | 22.7 | 21 | 57 |
| GI-20$_{X17}$ | GIKEXKRIVQRIKDFLRNLV | >40.6 | 7.3 | — | 58 |
| GI-20$_{W17}$ | GIKEWKRIVQRIKDFLRNLV | 7.4 | 23.6 | 3.2 | 59 |
| GI-20$_{Q16}$ | GIKQFKRIVQRIKDFLRNLV | 0.91 | 13.7 | 15.1 | 60 |
| GI-20$_{EF}$ | GIKEFKREFQRIKDFLRNLV | 1.6 | 9.9 | 6.2 | 61 |

[a]Although the standard errors from multiple antiviral assays are not provided, they were, on average, less than 10% of the respective mean $EC_{50}$ or $TC_{50}$.
[b]In the sequence of LL-37, the region used to engineer an optimal anti-HIV peptide (GI-20) is underlined. For all sequences, mutated residues are in boldface, and X represents phenylglycine.
[c]The incorporation of D-amino acids is indicated by d followed by the number of D-amino acids (in boldface).

Since a minimal antibacterial and anticancer peptide from LL-37 has been identified (Li et al. (2006) J. Am. Chem. Soc., 128:5776-5785), the anti-HIV activity of FK-13 was tested (Table 4). FK-13 displayed an effect on HIV with an $EC_{50}$ of 5.9 μg/mL (Table 4). However, when amino acid residue F17 (as numbered in LL-37) was removed from the peptide FK-13, the resultant peptide (KR-12 in Table 4) lost its anti-HIV activity ($EC_{50}$>100 μg/mL), indicating that F17 was essential for HIV inhibition and FK-13 was a minimal anti-HIV region of human LL-37. The anti-HIV-1 specificity of the minimal essential region of LL-37 was also confirmed by evaluating the activity of the peptide obtained by reversing the sequence of FK-13 (retro-FK13). This retro-FK13 peptide lost its activity against HIV ($EC_{50}$>100 μg/mL), but remained active against bacteria (Li et al. (2006) Biochim. Biophys. Acta 1758:1203-1214). Thus, there is no correlation between antibacterial and anti-HIV activities of these peptides as one might have expected.

To obtain peptide templates with improved TIs, additional peptides were designed on the basis of the sequence of FK-13. First, the sequence of FK-13 was extended at the C-terminus by restoring the three original residues of LL-37 (GF-17 in Table 4). Compared to human LL-37, the addition of the NLV segment led to an increase in activity against HIV ($EC_{50}$=2.0 μg/mL) as well as cytotoxicity to the human target cells ($TC_{50}$=18.7 μg/mL) (Table 4). In an attempt to improve the therapeutic index of GF-17, D-amino acids were also incorporated into the peptide at positions 24 and 28 (as numbered in LL-37). D-amino acid incorporation tends to reduce helicity (Li et al. (2006) J. Am. Chem. Soc., 128:5776-5785; Papo et al. (2004) Biochemistry 43:6393-6403). Surprisingly, these D-amino acid-containing peptides became inactive even when one D-amino acid was introduced (GF-17$_{d24}$ (GF-17$_{d1}$); Table 4). However, the cytotoxicity of the peptide to human cells dropped with an increase in the number of D-amino acids (GF-17$_{d24,d28}$ (GF-17$_{d2}$); Table 4).

Based on GF-17, an additional peptide was synthesized by restoring a short segment of LL-37 at the N-terminus. The positions between I13 and G14 (Wang, G. (2007) Biochim. Biophys. Acta, 1768:3271-3281; Wang, G. (2008) Open Magn. Reson. J., 1:9-15) were inverted to make glycine the first residue as is observed in numerous antimicrobial peptides collected in the antimicrobial peptide database (Wang et al. (2004) Nucleic Acids Res., 32:D590-D592). Compared to either LL-37 or GF-17, the resulting peptide GI-20 (Table 4) displayed an improved therapeutic index, indicating the importance of the additional four amino acid segment GIKE. To provide additional insight into the antiviral effect of specific residues in GI-20, some additional peptide mutants were synthesized. Of significant interest is that a change of F17 (i.e. the first residue after the GIKE segment) to a nonstandard amino acid phenylglycine (X, bold in Table 4), which differs from phenylalanine merely by a methylene ($CH_2$) group, led to the disruption of the anti-HIV activity of the peptide. Meanwhile, this peptide became more toxic to human target cells (Table 4). Likewise, a change of F17 to W also reduced the anti-HIV activity of the peptide without influencing the toxicity to human cells. These results further substantiated the essential role of F17 in human LL-37 in inhibiting HIV infection. Interestingly, when E16 of GI-20 was replaced with Q16, the peptide became more toxic to human cells but without any change in observed anti-HIV activity. Thus, E16 appeared to contribute to the selectivity of the peptide. Since F17 is critical for anti-HIV effect and E16 modulates the selectivity, the effect of this amino acid pair was also tested by substituting I19V20 for E19F20 (Table 4). While the antiviral efficacy of the resulting peptide reduced only slightly, cellular toxicity doubled relative to GI-20. Thus, it is clear that the F effect overrode the E effect in this particular case. These data indicate that both anti-HIV efficacy and cellular toxicity of GI-20 are subject to modulation, laying the basis for future peptide engineering.

To expand potentially useful peptide templates, the anti-HIV activity of BMAP-27-derived peptides were also evaluated. BMAP-27 is a 27-residue bovine cathelicidin peptide with the potential to form an α-helical conformation followed by a hydrophobic tail (Skerlavaj et al. (1996) J. Biol. Chem., 271:28375-28381). BMAP-18 (Table 5) was obtained by deleting the C-terminal hydrophobic tail of BMAP-27. Meanwhile, the leucine near the C-terminus was changed to an isoleucine residue to facilitate future NMR studies. BMAP-18 was found to be more active ($EC_{50}$=0.8 μg/mL, Table 5) against HIV but was also more toxic to human cells than GI-20 although the overall therapeutic index is slightly better (Table 4). However, further deletion of three residues from the C-terminus of BMAP-18 disrupted both the antiviral and cytotoxic effects of the resulting peptide (BMAP-15). Thus, additional mutational studies based on the minimal essential peptide BMAP-18 were performed. Changing the central two phenylalanines (F6 and F10) of BMAP-18 to phenylglycines slightly reduced anti-HIV activity. However, the peptide became inactive when the two phenylalanines were changed to isoleucine and leucine residues. These data indicate that the aromatic rings are critical for the anti-HIV activity of BMAP-18 as well. Furthermore, the antiviral effect was decreased when amino acid residue K9 of BMAP-18 was substituted by a proline residue. It is likely that the introduction of the proline distorted the potential helical structure of the peptide (Skerlavaj et al. (1996) J. Biol. Chem., 271:28375-28381), which might be critical for anti-HIV activity.

TABLE 5

Anti-HIV activities of *bovine* cathelicidin BMAP-27-derived peptides in CEM-SS cells[a].

| Peptide name | Peptide sequence[b] | $EC_{50}$ (µM) | $TC_{50}$ (µM) | TI | SEQ ID NO |
|---|---|---|---|---|---|
| BMAP-18 | GRFKRFRKKFKKLFKKIS | 0.35 | 8.45 | 24.1 | 62 |
| BMAP-18$_{P9}$ | GRFKRFRKPFKKLFKKIS | 3.20 | 18.9 | 5.9 | 63 |
| BMAP-18$_{X6X10}$ | GRFKRXRKKXKKLFKKIS | 0.68 | 10.2 | 15 | 64 |
| BMAP-18$_{I6L10}$ | GRFKRIRKKLKKLFKKIS | >44.0 | 2.79 | — | 65 |
| BMAP-15 | GRFKRFRKKFKKLFK | >49.6 | >49.6 | — | 66 |

[a]Although the standard errors from multiple antiviral assays are not provided, they were, on average, less than 10% of the respective mean $EC_{50}$ or $TC_{50}$.
[b]Mutated residues are in boldface, and X represents phenylglycine.

Cathelicidins are important host defense peptides in mammals, fish, and birds. While multiple cathelicidins have been identified in cow, horse, and sheep, only one cathelicidin has been found in humans (Wang et al. (2004) Nucleic Acids Res., 32:D590-D592; Zanetti, M. (2004) J. Leukoc. Biol., 75:39-48). Interestingly, human LL-37 could be cleaved into biologically active fragments in vivo. It has been shown that nearly all of the peptide fragments were capable of inhibiting Gram-positive bacterial growth (Murakami et al. (2004) J. Immunol., 172:3070-3077; Yamasaki et al. (2006) FASEB J., 20:2068-2080). They may also have an effect on fungi (Lopez-Garcia et al. (2005) J. Invest. Dermatol., 125:108-115). Antiviral evaluations with these peptide fragments have not been previously reported. It has been demonstrated herein for the first time that both the N-terminal (LL-23) and C-terminal (KR-20) fragments of LL-37 are inactive against HIV-1. Clearly, these two terminal peptides were not produced in order to protect humans from viral/HIV infection. Rather, they are bactericidal (Murakami et al. (2004) J. Immunol., 172:3070-3077; Yamasaki et al. (2006) FASEB J., 20:2068-2080) and may have other biological functions yet to be defined. Since the central fragment SK-21 of LL-37 is active against HIV, it is reasonable to predict that natural occurring LL-37 fragments KS-27, LL-29, KS-30, and RK-31 are active as well since they all contain the sequence of SK-21.

Because of the importance of human LL-37, a minimal antibacterial and anticancer region corresponding to residues 17-29 (FK-13) by NMR spectroscopy (Li et al. (2006) J. Am. Chem. Soc., 128:5776-5785) was determined. Remarkably, it is demonstrated herein that FK-13 is also a minimal anti-HIV peptide. Using this peptide as the backbone, GI-20 was identified, which has a therapeutic index twice that of LL-37. In comparison with other less active peptides such as KR-20 and KR-12 and by generating residue-specific mutants, it was also found that residue F17 is essential for inhibition of HIV replication. Taken together with the data obtained from the bovine peptides, it appears that aromatic phenylalanines in human and bovine cathelicidin peptides play an important role in blocking HIV-1 infection.

The entry of HIV-1 into a target T cell requires the binding of viral gp120/gp41 envelope glycoproteins to the cellular CD4 receptor and engagement of gp41 with the chemokine coreceptors (CXCR4 or CCR5) of the target cell (Stein et al. (1991) Adv. Exp. Med. Biol., 300:71-86), which precede the fusion of the viral and cellular membranes and introduction of the viral core into the cytoplasm to initiate infection. In the case of retrocyclin-1, its association with the C-terminal heptad repeat of gp41 prevents formation of the six-helix bundle structure of gp41 that mediates membrane fusion. Remarkably, this mechanism of HIV inhibition by retrocyclin-1 is similar to the peptide inhibitor T20 (Fuzeon®) which was designed based on gp-41 (Gallo et al. (2006) J. Biol. Chem., 281:18787-18792). Although it is not clear whether human cathelicidin peptides inhibit HIV-1 entry in a similar mechanism, it appears that a helical structure is required for viral targeting, since selective incorporation of D-amino acids into GF-17 led to the disruption of anti-HIV activity (Table 4). It was demonstrated that GI-20 adopted a helical conformation when in complex with detergent micelles (Li et al. (2006) J. Am. Chem. Soc., 128:5776-5785). Likewise, the anti-HIV effect of BMAP-18 reduced by nearly 9-fold when a proline was introduced (Table 5). Both D-amino acids (Li et al. (2006) J. Am. Chem. Soc., 128:5776-5785; Papo et al. (2004) Biochemistry 43:6393-6403) and prolines (Barlow et al. (1988) J. Mol. Biol., 201:601-619; Cordes et al. (2002) J. Mol. Biol., 323:951-960) are known to distort the regular geometry of helices.

In conclusion, the instant evaluation of 20 synthetic peptides derived from LL-37 and BMAP-27 led to the identification of the most important regions in both human and bovine cathelicidins active against HIV. Peptide sequence order, aromatic phenylalanine residues, and potential helical structures were found to play important roles in blocking HIV-1 infection. Because GI-20 and BMAP-18 have TIs superior to the TI of LL-37, they may now be used as novel anti-HIV microbicides as well as templates for the engineering of novel anti-HIV microbicides.

EXAMPLE 3

The antimicrobial peptide field is growing rapidly in response to the demand for novel antimicrobial agents (Zasloff, M. (2002) Nature, 415:389-395; Boman, H. G. (2003) J. Intern. Med., 254:197-215; Yamasaki et al. (2008) Eur. J. Dermatol., 18:11-21; Hancock et al. (2006) Nat. Biotechnol., 24:1551-1557; Daly et al. (2007) Biochemistry, 46:9920-9928). To promote the research, education and information exchange in the field, the multifunctional antimicrobial peptide database (APD) was established in 2003 and a brief description in the database issue of Nucleic Acid Research was published in 2004 (Wang and Wang (2004) Nucleic Acids Res., 32:D590-D592). Although there are other databases (Wade et al. (2002) Protein Pept. Lett., 9:53-57; Brahmachary et al. (2004) Nucleic Acids Res., 32:D586-D589; Whitmore et al. (2004) Nucleic Acids Res., 32:D593-

D594; Gueguen et al. (2006) Dev. Comp. Immunol., 30:283-288; Seebah et al. (2007) Nucleic Acids Res., 35:D265-D268; Fjell et al. (2007) Bioinformatics, 23:1148-1155; Hammami et al. (2007) BMC Microbiol., 7:89; Wang et al. (2008) Nucleic Acids Res., 36:D206-D210), the APD has been widely utilized by users around the world (~15 000 web hits per year; Wang, G. (2007) Protein Pept. Lett., 14:57-69; Loose et al. (2006) Nature, 443:867-869; Lata et al. (2007) BMC Bioinformatics, 8:263). The APD is a general database dedicated to antimicrobial peptides from all biological sources, ranging from bacteria, plants, to animals, including humans. The database collects only mature and active peptides (<100 amino acid residues), rather than a mixture of mature and precursor proteins. Furthermore, the peptides in the APD are classified based on their biological activities such as anticancer, antiviral, antifungal and antibacterial, allowing users to readily obtain a list of peptides of special interest to them. In addition, the database provides statistical information for all listed peptides, or a group of peptides with desired properties such as anticancer. Finally, the database has interfaces for both peptide prediction and peptide design. The APD also provides 'Links' that allow users to access other databases dedicated to antimicrobial peptides.

Since the publication of the first version of the APD in 2004, a significant number of antimicrobial peptides have been discovered at both the gene and protein levels. Therefore, it is proper to include the newly identified members into the APD. In total, more than 700 additional peptides have been registered into the second version of the database. To meet the new requirements of the field as well as based on users' feedback, additional search capabilities have been constructed for the database. These include peptide families, sources, posttranslational modified peptides, and peptide-binding targets. Finally, it is illustrated that novel antimicrobial peptides can be designed with the aid of the APD. Among the three peptides designed, one of them showed a higher activity against *Escherichia coli* than human LL-37. Here, the new features and findings of the second version of the APD (hereinafter referred to as the APD2) are described.

Database Update

To facilitate database update and maintenance, the NAVICAT 8 software (PremiumSoft™ CyberTech Limited, Hong Kong) was used to solve the compatibility problem with the database by writing additional programs. These programs also enable a recalculation of peptide parameters should the original peptide sequence have been corrected, updated or completely replaced. By September 2008, the APD2 possessed 1228 peptide entries. Relative to the original 525 entries, the total number of antimicrobial peptides in the APD2 has been more than doubled. Among them, the number of antibacterial peptides increased from 498 to 944 (i.e. by 90%), antifungal peptides from 155 to 327 (by 111%), antiviral peptides from 28 to 76 (by 171%) and anticancer peptides from 18 to 65 (by 261%). It appears that the interest in developing antiviral and anticancer peptides on the basis of naturally occurring antimicrobial peptides is growing (Hoskin et al. (2008) Biochim. Biophys. Acta, 1778:357-375; Cole et al. (2008) Am. J. Reprod. Immunol., 59:27-34; Wang et al. (2008) Antimicrob. Agents Chemother., 52:3438-3440).

New Features Added

The 'name' field of the APD2 has been expanded significantly through extensive information registration. Peptide synonyms such as LL-37 and LL37 are included. This feature should benefit the ongoing effort in standardizing the nomenclature of antimicrobial peptides from amphibians (Conlon, J. M. (2008) Peptides, 29:1631-1632; Amiche et al. (2008) Peptides, 29:2074-82). Because both the old and new names of the same peptides are entered, the APD2 will facilitate the transition from the old to the new names.

Not all antimicrobial peptides have complete amino acid sequences. A list of peptides with incomplete amino acid sequences can be viewed by entering the letter string 'BWQ' into the name field followed by clicking on the 'search' button. Currently, the APD2 collects 18 such entries.

The APD2 allows the search for peptides from a particular life form by using common names: 'bacteria, plant, ants, fish, cow, insect, crabs, toad and frog' (actual words for search), to list just a few. For example, when the word 'frog' was searched in the name field, 398 peptides (32% in the APD2) appeared, consistent with the notion that amphibians are an important source for natural antimicrobial peptides (Zasloff, M. (2002) Nature, 415:389-395; Conlon, J. M. (2008) Peptides, 29:1631-1632; Amiche et al. (2008) Peptides, 29:2074-82). Similarly, 203 peptides from plants, 118 from insects and 112 from bacteria were found. Therefore, the majority of the naturally occurring antimicrobial peptides collected in the APD2 are originated from animals. To advance the understanding of the structure-activity relationships of antimicrobial peptides as a basis for peptide design, a select set of synthetic peptide derivatives were also collected. After update, the database contains 38 synthetic peptides (3% in the APD2). Most of the synthetic peptides have known 3D structures, determined primarily by solution NMR spectroscopy (Epand et al. (1999) Biochim. Biophys. Acta, 1462:11-28; Wang, G. (2006) Curr. Org. Chem., 10:569-581). In total, there are 160 peptides (152 by NMR and eight by X-ray diffraction) with known 3D structures (70 originally). As long as the structural coordinates are deposited with the Protein Data Bank (PDB) (Berman et al. (2000) Nucleic Acids Res., 28:235-242), the structure of a particular peptide can be viewed directly by clicking on the PDB link provided in the APD2 for each peptide entry.

In addition, 'peptide families' can be searched, also via the name field. When the word 'cyclotide' (small circular proteins from plants) (Cole et al. (2008) Am. J. Reprod. Immunol., 59:27-34) was entered, 126 peptides appeared. Likewise, 131 defensins and 51 cathelicidins were found when such words were searched.

To allow for the search for 'chemically modified antimicrobial peptides', a coding system was created by starting with XX. Thus, phosphorylation, lipidation, glycosylation, C-terminal amidation, peptide cyclization, oxidation and D-amino acids are represented by a set of unique letter strings. Such modifications are described in the 'Additional Info' field so that the unmodified peptide sequence can be entered into the database. In total, 259 chemically modified peptides were found when XX was used to search in the name field. Among them, 135 peptides are cyclic, 113 peptides are C-terminally amidated (XXA), seven peptides are oxidized (XXO), and nine peptides contain D-amino acids (XXD). The number of D-amino acid residues in a peptide is indicated by an Arabic number after the code XXD. Note that the actual numbers of chemically modified peptides in the database will vary due to continued updating of the database.

It is now accepted that 'molecular targets' of antimicrobial peptides are not restricted to bacterial membranes and can be other molecules as well (Zasloff, M. (2002) Nature, 415:389-395; Boman, H. G. (2003) J. Intern. Med., 254:197-215; Yamasaki et al. (2008) Eur. J. Dermatol., 18:11-21; Hancock et al. (2006) Nat. Biotechnol., 24:1551-1557; Daly et al. (2007) Biochemistry, 46:9920-9928). To enable the search for peptide targets, a set of unique letter strings (starting BB) was defined for different targets such as proteins, nucleic acids, sugars and metal ions and entered such information into the database. A typical example is human LL-37, which is capable of binding to a variety of molecules such as proteins (represented by BBPP), DNA (BBD) and lipopolysaccharides or LPS (BBL) (Wang, G. (2007) Protein Pept. Lett., 14:57-69). In addition, the peptide is able to form oligomers by itself (BBB) in aqueous solutions upon increase in peptide concentrations or salts. Likewise, the string BBBm is coined as an indicator for peptide oligomerization in membrane environments. A further description of the interactions between antimicrobial peptides and different targets is given in the field of 'Additional Info' (e.g. see entry 310 for LL-37). This change will enrich the key information on biochemical and physical property, activity, 3D structure and mechanism of action of each antimicrobial peptide in the APD2.

It is also useful to search for peptides that target a particular microbe by using the letter 'Z'. When 'ZZH' was used to search, 53 anti-HIV peptides appeared. A further classification of the peptide sources was also made: ZZHa, anti-HIV peptides from animals (14 entries); ZZHb, anti-HIV peptides from bacteria (three entries); ZZHp, anti-HIV peptides from plants (24 entries, mainly cyclotides); ZZHh, anti-HIV peptides from humans (six entries); ZZHs, anti-HIV peptides from chemical synthesis (six entries). Additional letters can be appended to indicate the binding targets of HIV-active peptides. Such a feature is useful for users to choose a peptide template for engineering anti-HIV peptides by mutagenesis (Wang et al. (2008) Antimicrob. Agents Chemother., 52:3438-3440). Likewise, future database annotations will allow users to search for peptides with toxicity against a particular drug-resistant bacterial strain (ZZB), parasites (ZZP), or certain type of cancer cells (ZZC).

Frequently Used Amino Acid Residues in Antimicrobial Peptides

The search capability for peptide sources, families, and activities can be combined with the peptide analysis tools in the APD2. A statistical analysis was conducted for a group of peptides from bacteria, plants, insects, and frogs. These life kingdoms were chosen because of a relatively large pool of peptides (>100 members). The percentages for the 20 amino acids in each group of peptides from the four kingdoms was plotted. A residue in antimicrobial peptides is defined as 'frequently used' if its percentage is ~10% or greater. Thus, residues Ala and Gly are most abundant in bacterial peptides; residues Cys and Gly are more common in plant peptides; residues Ala, Gly and Lys are frequently occurring in insect peptides; and residues Leu, Ala, Gly and Lys have percentages higher than 10% in frog peptides. It is notable that residue Gly is highly used in antimicrobial peptides from all the four kingdoms. In contrast, residue Met is rarely used (<1.5%). Interestingly, cationic Lys is preferred over Arg in all the kingdoms. In particular, residues Arg and Tyr are rarely used (<1%) in frog peptides. However, the lists of highly used residues derived from antimicrobial peptides from different kingdoms contain structural information. The abundance in residue Cys in plant peptides suggests that disulfide bonds (related to β-sheets) are common, rendering the peptide structure more stable (Cole et al. (2008) Am. J. Reprod. Immunol., 59:27-34). Indeed, the percentage of the Cys residue is also high in peptides with known β-sheet structures. Likewise, the frequently used residues from frogs (Leu, Ala, Gly and Lys) have the strong tendency to adopt an amphipathic helix. Interestingly, a search of the APD2 for antimicrobial peptides with known helical structures followed by statistical analysis of the 170 peptides revealed the same set of frequently occurring residues.

Database-Aided Peptide Design

The frequently used residues identified in each kingdom may be applied to peptide design in different ways. First, new antimicrobial peptides can be designed based on 'templates derived from naturally occurring antimicrobial peptides'. Recently, the smallest antibacterial peptide, KR-12, from human LL-37 was identified (Wang, G. (2008) J. Biol. Chem., 283:32637-32643). Using KR-12 as the template, KL-12 (KKLLKKLKKLLK; SEQ ID NO: 67) was designed by converting all hydrophobic residues to leucines and all charged and hydrophilic residues to lysines. Unfortunately, antibacterial assays using the standard microdilution method (Wang et al. (2005) J. Biol. Chem., 280:5803-5811) found that KL-12 was inactive against Gram-negative bacteria such as *E. coli* K12 or Gram-positive bacteria such as methicin-resistant *Staphylococcus aureus* (MRSA) USA-300 until 160 mM. However, this method may be successful with other more active peptide templates. Second, new antimicrobial peptides can be designed by 'combining database-derived peptide motifs', consisting of frequently used residues. Using the motifs consisting of only residues Gly, Leu and Lys, a second peptide was designed. GLK-19 (GLKKLLGKLLKKLGKLLLK; SEQ ID NO: 46) was found to be active against *E. coli* ($IC_{50}$=10 µM) and also weakly active against MRSA ($IC_{50}$=160 µM). Third, new peptides can be designed based on 'amino acid percentages obtained from statistical analysis of antimicrobial peptides' from a specific kingdom or peptide family. Thus, a third peptide was designed in three steps. (i) The amino acid composition for MULTI-18 was obtained by multiplying the percentage of each residue with the total number of residues (18 here) in the target peptide. Thus, 2 Gly, 2 Ala, 3 Leu, 3 Lys, 2 Ile, 1 Phe, 1 Asp, 1 Val, 1 Thr, 1 Ser and 1 Asn residues were obtained based on the statistical values obtained. (ii) Peptide motifs, consisting of these residues and found that sequence combinations such as GLFD, AAK, KIV, GKL, ITS and LN all exist in at least five peptides in the APD2, were searched. (iii) Multiple peptides can be obtained by combining the above motifs. Only one peptide was designed by following the amphipathic pattern for helical peptides. The resulting peptide MULTI-18 (GLFDAAKKIVGKLITSLN; SEQ ID NO: 68) showed a low activity against *E. coli* ($IC_{50}$=80 µM). Although only three peptides were designed, one of the peptides (GLK-19) was found to have a higher antibacterial activity against *E. coli* than human LL-37. Therefore, the results prove the principle that the APD2 is a useful tool for peptide design. In the previous version of the database, it was observed that antimicrobial peptides with toxic effects on mammalian cells are more hydrophobic. That finding, consistent with the results from experiments (Li et al. (2006) J. Am. Chem. Soc., 128:5776-5785), should be useful in improving the therapeutic indexes of the designed peptides such as GLK-19 in the next step.

The database update increased the number of antimicrobial peptides from 525 to 1228. This increase improves the reliability of the results from the statistical interface. New search capabilities such as peptide families, peptide sources and anti-HIV activity have been created via extensive information annotations and registration for peptide entries. In addition, both chemically modified peptides and molecular targets of antimicrobial peptides can be searched. In combination with the statistical interface, it was found that frequently used amino acid residues in antimicrobial peptides differ in different kingdoms. Using the frequently occurring residues from amphibian peptides, it was demonstrated that the APD2 findings are useful in peptide design.

A number of publications and patent documents are cited throughout the foregoing specification in order to describe the state of the art to which this invention pertains. The entire disclosure of each of these citations is incorporated by reference herein.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. An isolated anti-HIV peptide comprising SEQ ID NO: 45 or a variant of SEQ ID NO: 45 wherein lysine is substituted with arginine.

2. The isolated anti-HIV peptide of claim 1, wherein said peptide comprises SEQ ID NO: 45.

3. An isolated anti-HIV peptide comprising SEQ ID NO: 45 or a variant of SEQ ID NO: 45 wherein lysine is substituted with arginine, wherein at least one amino acid is a D-amino acid.

4. The isolated anti-HIV peptide of claim 1, wherein said peptide comprises at least one modification selected from the group consisting of amidation and acetylation.

5. A composition comprising at least one anti-HIV peptide of claim 1 and at least one pharmaceutically acceptable carrier.

6. The composition of claim 5, further comprising at least one anti-HIV compound.

7. The composition of claim 6, wherein said anti-HIV compound is selected from the group consisting of nucleoside-analog reverse transcriptase inhibitors, non-nucleoside reverse transcriptase inhibitors, protease inhibitors, fusion inhibitors, antibodies, and vaccines.

8. A method for inhibiting an HIV infection in a subject in need thereof, said method comprising administering to said subject the composition of claim 5.

9. The method of claim 8, further comprising the administration of at least one additional anti-HIV compound.

10. The isolated anti-HIV peptide of claim 2, wherein the amino acid sequence of said peptide is SEQ ID NO: 45.

11. The isolated anti-HIV peptide of claim 3, wherein said peptide comprises SEQ ID NO: 45, and wherein at least one amino acid is a D-amino acid.

12. The isolated anti-HIV peptide of claim 3, wherein said peptide comprises at least one modification selected from the group consisting of amidation and acetylation.

13. A composition comprising at least one anti-HIV peptide of claim 3 and at least one pharmaceutically acceptable carrier.

14. The composition of claim 13, further comprising at least one anti-HIV compound.

15. The composition of claim 13, wherein said anti-HIV compound is selected from the group consisting of nucleoside-analog reverse transcriptase inhibitors, non-nucleoside reverse transcriptase inhibitors, protease inhibitors, fusion inhibitors, antibodies, and vaccines.

16. A method for inhibiting an HIV infection in a subject in need thereof, said method comprising administering to said subject the composition of claim 13.

17. The method of claim 16, further comprising the administration of at least one additional anti-HIV compound.

* * * * *